United States Patent
Leedman et al.

(10) Patent No.: US 9,795,626 B2
(45) Date of Patent: Oct. 24, 2017

(54) CANCER THERAPY USING MIRNAS

(71) Applicant: THE UNIVERSITY OF WESTERN AUSTRALIA, Nedlands, WA (US)

(72) Inventors: Peter Jeffery Leedman, Mount Claremont (AU); Keith Michael Giles, Mullaloo (AU); Rikki Ann Mary Brown, Nollamara (AU)

(73) Assignee: The University of Western Australia, Western Australia (AU)

( * ) Notice: Subject to any disclaimer, the term of this patent is extended or adjusted under 35 U.S.C. 154(b) by 20 days.

(21) Appl. No.: 14/436,638

(22) PCT Filed: Oct. 18, 2013

(86) PCT No.: PCT/AU2013/001208
§ 371 (c)(1),
(2) Date: Apr. 17, 2015

(87) PCT Pub. No.: WO2014/059484
PCT Pub. Date: Apr. 24, 2014

(65) Prior Publication Data
US 2015/0366895 A1    Dec. 24, 2015

(30) Foreign Application Priority Data
Oct. 18, 2012 (AU) ................ 2012904570

(51) Int. Cl.
*A61K 48/00* (2006.01)
*A61K 31/7105* (2006.01)
*A61K 45/06* (2006.01)
*A61K 31/365* (2006.01)
*A61K 31/4188* (2006.01)
*A61K 31/437* (2006.01)
*A61K 31/519* (2006.01)
*A61K 31/495* (2006.01)

(52) U.S. Cl.
CPC ........ *A61K 31/7105* (2013.01); *A61K 31/365* (2013.01); *A61K 31/4188* (2013.01); *A61K 31/437* (2013.01); *A61K 31/495* (2013.01); *A61K 31/519* (2013.01); *A61K 45/06* (2013.01)

(58) Field of Classification Search
None
See application file for complete search history.

(56) References Cited

FOREIGN PATENT DOCUMENTS

WO   WO 2007/081740   7/2007
WO   WO 2011/063456   6/2011

OTHER PUBLICATIONS

Variant. (n.d.). Dictionary.com Unabridged. Retrieved Mar. 16, 2017 from Dictionary.com website http://www.dictionary.com/browse/variant.*
Thatcher et al. (GMC Genomics, 2008 vol. 9:253, pp. 1-9.*
(Continued)

*Primary Examiner* — Terra C Gibbs
(74) *Attorney, Agent, or Firm* — Seyfarth Shaw LLP

(57) ABSTRACT

The present invention relates generally to methods and compositions for the treatment of cancers expressing the type 1 insulin-like growth factor receptor (IGF1R) or a constituent of an IGF1R signaling pathway, in particular melanoma, using the microRNA miR-7-5p. Also provided are methods for increasing the sensitivity of such cancers to therapeutic agents.

11 Claims, 13 Drawing Sheets

(56) References Cited

OTHER PUBLICATIONS

Bollag, Gideon, et al.: "Vemurafenib: the first drug approved for BRAF-mutant cancer", doi: 10.1038/nrd3847, published online Oct. 12, 2012.

Chapman, Paul B., et al.: "Improved Survival with Vemurafenib in Melanoma with BRAF V600E Mutation", The New England Journal of Medicine, vol. 364(26), pp. 2507-2516, Jun. 30, 2011.

Zhao, X., et al.: "MicroRNA-7 functions as an anti-metastatic microRNA in gastric cancer by targeting insulin-like growth factor-1 receptor", Oncogene, vol. 32, pp. 1363-1372, 2013.

L. Jiang et al., "MicroRNA-7 targets IGF1R (insulin-like growth factor 1 receptor) in tongue squamous cell carcinoma cells," *Biochem. J.*, 432: (1), 199-205 (2010).

K. Rai et al., "Liposomal delivery of microRNA-7 expressing plasmid overcomes epidermal growth factor receptor tyrosine kinase inhibitor-resistance in lung cancer cells," *Mol. Cancer Ther.* 10: (9), 1720-1727 (2011).

K.M. Giles et al., "mIRNA-7-5p inhibits melanoma cell migration and invasion," *Biochemical and Biophysical Research Communications*, 430: 706-710 (2013).

Ah, Yeh, et al.: "Human melanoma cells expressing V600E B-RAF Are susceptible to IGF1R targeting by small interfering RNAs", Oncogene, vol. 25, May 22, 2006, pp. 6571-6581.

The First Office Action issued in Chinese Patent Application No. 201380065503.0 on Dec. 6, 2016.

Pogribny, Igor P., et al.: "Alterations of microRNAs and their targets are associated with acquired resistance of MCF-7 breast cancer cells to cisplatin", International Journal of Cancer, vol. 127(8), Oct. 15, 2010, pp. 1785-1794.

European Search Opinion issued in European Patent Application No. 13 847 499.4 on Nov. 2, 2016.

* cited by examiner

A

B

A

B

A

B

SEQUENCE LISTING

```
<160> NUMBER OF SEQ ID NOS: 5

<210> SEQ ID NO 1
<211> LENGTH: 23
<212> TYPE: RNA
<213> ORGANISM: Homo sapiens

<400> SEQUENCE: 1
uggaagacua gugauuugu ugu                                         23

<210> SEQ ID NO 2
<211> LENGTH: 110
<212> TYPE: RNA
<213> ORGANISM: Homo sapiens

<400> SEQUENCE: 2
uuggauguug gccuaguucu guguggaaga cuagugauuu uguuguuuuu agauaacuaa    60
aucgacaaca aaucacaguc ugccauaugg cacaggccau gccucuacag              110

<210> SEQ ID NO 3
<211> LENGTH: 110
<212> TYPE: RNA
<213> ORGANISM: Homo sapiens

<400> SEQUENCE: 3
cuggauacag aguggaccgg cuggccccau cuggaagacu agugauuug uuguugucuu     60 acugcgcuca acaacaaauc ccagucuacc uaauggugcc agccaucgca              110

<210> SEQ ID NO 4
<211> LENGTH: 110
<212> TYPE: RNA
<213> ORGANISM: Homo sapiens

<400> SEQUENCE: 4
agauuagagu ggcugugguc uagugcugug uggaagacua gugauuugu uguucugaug    60 uacuacgaca acaagucaca gccggccuca uagcgcagac ucccuucgac              110

<210> SEQ ID NO 5
<211> LENGTH: 6
<212> TYPE: RNA
<213> ORGANISM: Artificial sequence
<220> FEATURE:
<223> OTHER INFORMATION: Synthteic Oligonucleotide

<400> SEQUENCE: 5 ggaaga                                                              6
```

CANCER THERAPY USING MIRNAS

This application is a National Stage of PCT/AU2013/069633, filed Oct. 18, 2013, which claims benefit of Australian Patent Application No. 2012904570, filed Oct. 18, 2012, the disclosures of which are incorporated herein by reference in their entirety.

FIELD OF THE INVENTION

The present invention relates generally to methods and compositions for the treatment of cancers expressing the type 1 insulin-like growth factor receptor (IGF1R) or a constituent of an IGF1R signaling pathway, in particular melanoma, using the microRNA miR-7-5p. Also provided are methods for increasing the sensitivity of such cancers to therapeutic agents.

RELATED APPLICATIONS

This application claims priority to Australian Provisional Application No. 2012904570, entitled "Cancer Therapy Using miRNAs", filed on 18 Oct. 2012. The subject matter of Australian Provisional Application No. 2012904570 is incorporated herein by reference in its entirety.

The instant application contains a Sequence Listing which has been submitted in ASCII format via EFS-Web and is hereby incorporated by reference in its entirety. Said ASCII copy, created on Apr. 17, 2015, is named 01580003US1.txt and is 1.38 kilobytes in size.

BACKGROUND OF THE INVENTION

Melanoma is the most aggressive form of skin cancer and is an increasing health problem around the world, with incidence rates on the rise year on year. Once melanoma has metastasised there are few effective treatments, and mortality is high. Melanoma is capable of rapid metastasis and is often refractory to conventional chemotherapy and radiotherapy. This resistance is a major obstacle to improving patient survival and with the paucity of effective therapeutic agents, there exists a need to develop novel, therapeutically effective approaches to treat melanoma.

Increased understanding of the molecular biology of melanoma, including the identification of gene mutations as potential drug targets and of specific signaling pathways activated in melanoma, such as the insulin like growth factor 1 receptor (IGF1R) pathway, offers hope for the development of improved therapies. IGF1R is overexpressed in malignant melanoma compared to benign naevi and mediates processes such as survival, proliferation and motility. IGF1R stimulation leads to activation of two main downstream signaling pathways: the PI3K-Akt-TOR pathway and the Ras-Raf-MEK-ERK pathway, both of which are important for melanoma pathogenesis. Mutations occur in critical molecules of these pathways including NRAS (9-15% of melanomas), BRAF (66% of melanomas) and PTEN (30-60% of melanomas), resulting in constitutive activation of the pathways, promoting cell proliferation, survival, migration and invasion. While recent clinical trials with the mutant BRAF inhibitor PLX4032 (RG7204/Vemurafenib/Zelboraf®) have produced dramatic shrinkage of metastatic melanoma tumours, virtually all patients develop resistance. Importantly, upregulation of IGF1R signaling is a mechanism of ERK-independent resistance to BRAF inhibition. Thus, IGF1R and its downstream signaling pathways are potential targets for cancer therapy.

MicroRNAs (miRNAs) are a class of highly conserved, small (typically 21-25 nucleotides) non-coding RNAs that regulate both mRNA degradation and translation, at least partially through their ability to bind to the 3'-UTR of target genes via a 'seed region' of the miRNA. miRNAs are generated from RNA precursors (pri-miRNAs) that usually contain several hundred nucleotides transcribed from regions of non-coding DNA. Pri-miRNAs are processed in the nucleus by RNase III endonuclease to form stem-loop precursors (pre-miRNAs) of approximately 70 nucleotides. Pre-miRNAs are actively transported into the cytoplasm where they are further processed into short RNA duplexes, typically of 21-23 nucleotides. The functional miRNA strand dissociates from its complementary non-functional strand and locates within, the RNA-induced-silencing-complex (RISC). (Alternatively, RISC can directly load pre-miRNA hairpin structures.) miRNAs bind the 3'UTRs of target mRNAs and important in this binding is a 'seed region' of approximately 6-7 nucleotides near the 5' end of the miRNA (typically nucleotide positions 2 to 8). miRNA-induced regulation of gene expression is typically achieved by translational repression, either degrading proteins as they emerge from ribosomes or 'freezing' ribosomes, and/or promoting the movement of target mRNAs into sites of RNA destruction.

miRNAs are crucial to many normal cellular functions and are involved in processes such as stem cell division, embryonic development, cellular differentiation, inflammation and immunity. Increasingly, specific miRNAs, and expression patterns and altered regulation of expression of individual miRNAs, are also being implicated in a variety of disease conditions, including cancer. miR-7-5p is characterized as a tumour suppressor miRNA in several cancer types, where it targets and represses molecules such as IGF1R (insulin like growth factor 1 receptor), PAK1 (p21-activated kinase 1), IRS-1/2 (insulin receptor substrates 1 and 2), EGFR (epidermal growth factor receptor), FAK (focal adhesion kinase) and RAF1 (v-raf-1 murine leukaemia viral oncogene homologue 1).

SUMMARY OF THE INVENTION

In a first aspect the present invention provides a synergistic composition for the treatment of a cancer or tumour expressing IGF1R or a constituent of an IGF1R signaling pathway, the composition comprising a miR-7-5p miRNA, a precursor or variant thereof or a miRNA comprising a seed region comprising the sequence GGAAGA, and at least one of a BRAF inhibitor, an IGF1R inhibitor and a DNA alkylating chemotherapeutic agent.

In a particular embodiment, the cancer is melanoma. The melanoma may be malignant melanoma. The melanoma may comprise cells expressing a mutation in one or more of BRAF, NRAS or PTEN.

The miR-7-5p miRNA may be hsa-miR-7-5p and may comprise the nucleotide sequence set forth in SEQ ID NO:1. The miR-7-5p miRNA precursor may be selected from hsa-miR-7-1, hsa-miR-7-2 and hsa-miR-7-3, and may comprise a sequence as set forth in any one of SEQ ID Nos: 2 to 4.

The BRAF inhibitor may be a mutant BRAF—specific inhibitor or mutant BRAF—selective inhibitor. The mutant BRAF may comprise, for example, the V600E, V600D, V600K or V600R mutation. In a particular embodiment, the BRAF inhibitor is PLX4032 (vemurafenib; such as Zelboraf®). In a particular embodiment, the IGF1R inhibitor is a tyrosine kinase inhibitor, and may be selected from picropodophyllin (PPP) and NVP-AEW541. In a particular embodiment, the chemotherapeutic agent is temozolomide (TMZ; such as Temodar®).

A second aspect of the invention provides a method for treating a cancer or tumour expressing IGF1R or a constituent of an IGF1R signaling pathway in a subject, comprising administering to the subject synergistically effective amounts of a miR-7-5p miRNA, a precursor or variant thereof or a miRNA comprising a seed region comprising the sequence GGAAGA, and at least one therapeutic agent selected from of a BRAF inhibitor, an IGF1R inhibitor and a DNA alkylating chemotherapeutic agent.

The therapeutic agent and the miRNA may be administered in a single composition, formulated together with pharmaceutically acceptable carriers, excipients or adjuvants or may be administered in separate compositions. In one embodiment the method comprises administering to the subject an effective amount of a composition of the first aspect. Where the agents are administered separately administration may be simultaneous or sequential. In particular embodiments, administration of the miRNA renders the cancer susceptible to a cytostatic or cytotoxic dose of the therapeutic agent that is lower than the cytostatic or cytotoxic dose required in the absence of the miRNA. Accordingly, where administration is sequential typically the miRNA is administered prior to the therapeutic agent.

A third aspect of the invention provides a method for sensitising a cancer or tumour cell expressing IGF1R or a constituent of an IGF1R signaling pathway to a therapeutic agent selected from a BRAF inhibitor, an IGF1R inhibitor and a DNA alkylating chemotherapeutic agent, the method comprising contacting the cell with an effective amount of a miR-7-5p miRNA, a precursor or variant thereof or a miRNA comprising a seed region comprising the sequence GGAAGA.

The cancer or tumour cell, or the cancer or tumour from which the cell is derived may display resistance to the therapeutic agent in the absence of treatment. The resistance displayed may be intrinsic resistance or acquired resistance.

Typically the sensitization renders the cell susceptible to a cytostatic or cytotoxic dose of the therapeutic agent that is lower than the cytostatic or cytotoxic dose required in the absence of the miRNA.

A fourth aspect of the invention provides a method for inhibiting or preventing cancer metastasis or cancer cell migration, wherein the cancer expresses IGF1R or a constituent of an IGF1R signaling pathway, the method comprising administering to a subject in need thereof and effective amount of a miR-7-5p miRNA, a precursor or variant thereof or a miRNA comprising a seed region comprising the sequence GGAAGA.

Typically in accordance with the above aspects and embodiments the miRNA inhibits the expression of one or more of insulin receptor substrate 2 (IRS-2), p21-activated kinase 1 (PAK1) and focal adhesion kinase (FAK).

Also provided herein is the use of a miR-7-5p miRNA, a precursor or variant thereof or a miRNA comprising a seed region comprising the sequence GGAAGA, and at least one therapeutic agent selected from of a BRAF inhibitor, an IGF1R inhibitor and a chemotherapeutic agent for the treatment of a cancer or tumour expressing IGF1R or a constituent of an IGF1R signaling pathway.

Also provided herein is the use of a miR-7-5p miRNA, a precursor or variant thereof or a miRNA comprising a seed region comprising the sequence GGAAGA for sensitising a cancer or tumour cell expressing IGF1R or a constituent of an IGF1R signaling pathway to a therapeutic agent selected from a BRAF inhibitor, an IGF1R inhibitor and a DNA alkylating chemotherapeutic agent.

Also provided herein is the use of a miR-7-5p miRNA, a precursor or variant thereof or a miRNA comprising a seed region comprising the sequence GGAAGA for inhibiting or preventing cancer metastasis or cancer cell migration, wherein the cancer expresses IGF1R or a constituent of an IGF1R signaling pathway.

BRIEF DESCRIPTION OF THE DRAWINGS

Embodiments of the invention are described herein, by way of non-limiting example only, with reference to the following figures.

Figure 1:
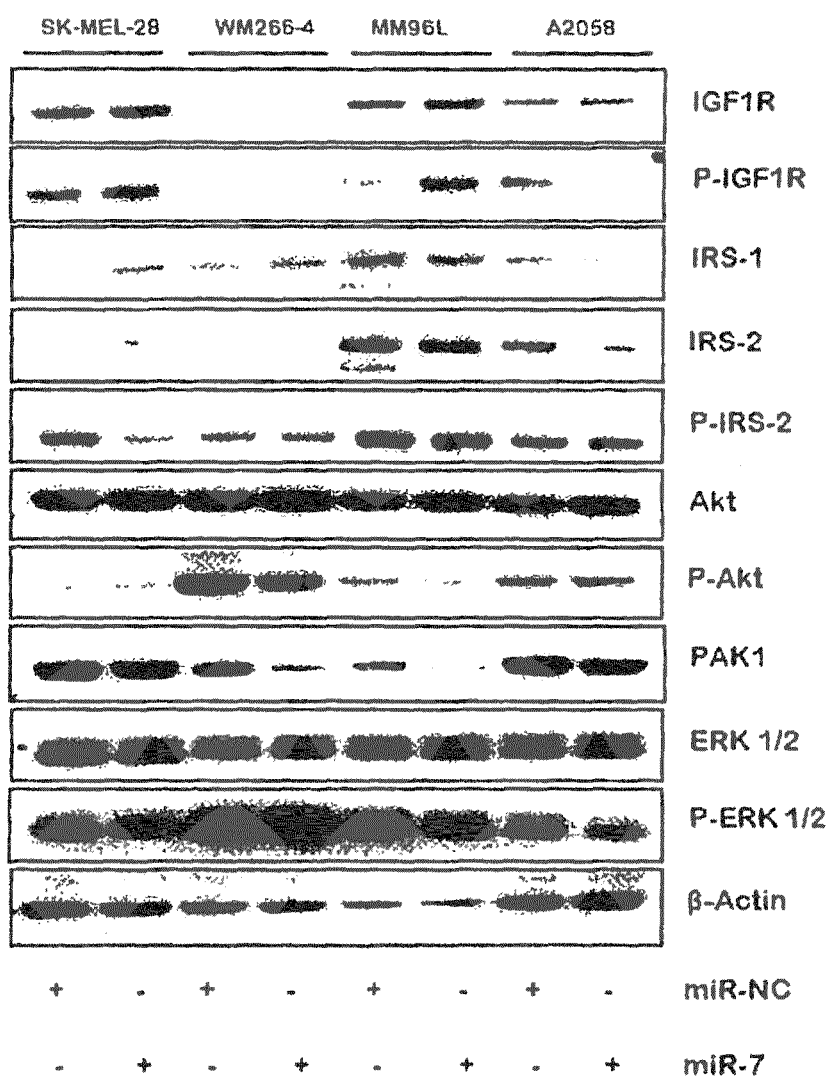
FIG. 1. miR-7-5p reduces expression of molecules of the IGF1R pathway and abrogates activation of Akt and ERK1/2 signalling in melanoma cells. Immunoblotting detection of indicated proteins using protein extracts harvested from SK-MEL-28, WM266-4, MM96L and A2058 melanoma cell lines transfected with miR-NC or miR-7-5p precursors at 15 nM (3 days post-transfection). β-Actin, loading control. Data is representative of three independent experiments.

A listing of nucleotide sequences corresponding to the sequence identifiers referred to in the specification is provided. The nucleotide sequences of mature human miR-7-5p, human miR-7-5p precursors and seed region are set forth in SEQ ID Nos: 1 to 5.

DETAILED DESCRIPTION

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein the term "oligonucleotide" refers to a single-stranded sequence of ribonucleotide or deoxyribonucleotide bases, known analogues of natural nucleotides, or mixtures thereof. An "oligonucleotide" comprises a nucleic-acid based molecule including DNA, RNA, PNA, LNA or any combination thereof. An oligonucleotide that predominantly comprises ribonucleotide bases, natural or non-natural, may be referred to as an RNA oligonucleotide. Oligonucleotides are typically short (for example less than 50 nucleotides in length) sequences that may be prepared by any suitable method, including, for example, direct chemical synthesis or cloning and restriction of appropriate sequences. "Antisense oligonucleotides" are oligonucleotides complementary to a specific DNA or RNA sequence. Typically in the context of the present invention an antisense oligonucleotide is an RNA oligonucleotide complementary to a specific miRNA. The antisense oligonucleotide binds to and silences or represses, partially of fully, the activity of its complementary miRNA. Not all bases in an antisense oligonucleotide need be complementary to the 'target' or miRNA sequence; the oligonucleotide need only contain sufficient complementary bases to enable the oligonucleotide to recognise the target. An oligonucleotide may also include additional bases. The antisense oligonucleotide sequence may be an unmodified ribonucleotide sequence or may be chemically modified or conjugated by a variety of means as described herein.

The term "polynucleotide" as used herein refers to a single- or double-stranded polymer of deoxyribonucleotide, ribonucleotide bases or known analogues of natural nucleotides, or mixtures thereof. A "polynucleotide" comprises a nucleic-acid based molecule including DNA, RNA, PNA, LNA or any combination thereof. The term includes reference to the specified sequence as well as to the sequence complimentary thereto, unless otherwise indicated. Polynucleotides may be chemically modified by a variety of means known to those skilled in the art. Thus a "polynucleotide" comprises a nucleic-acid based molecule including DNA, RNA, PNA, LNA or any combination thereof.

The term "sequence identity or "percentage of sequence identity" may be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences.

As used herein the terms "treating" and "treatment" and grammatical equivalents refer to any and all uses which remedy a condition or symptoms, prevent the establishment of a condition or disease, or otherwise prevent, hinder, retard, or reverse the progression of a condition or disease or other undesirable symptoms in any way whatsoever. Thus the term "treating" is to be considered in its broadest context. For example, treatment does not necessarily imply that a patient is treated until total recovery. In conditions which display or a characterized by multiple symptoms, the treatment need not necessarily remedy, prevent, hinder, retard, or reverse all of said symptoms, but may prevent, hinder, retard, or reverse one or more of said symptoms.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein, the term "synergistically effective amount" as applied to the combination of miR-7-5p or a precursor thereof and an additional therapeutic agent refers to the amount of each component which, in combination, is effective in inhibiting growth, or reducing viability, of cancer cells, and which produces a response greater than either component alone.

As used herein the term "IGF1R signaling pathway" refers to any pathway, typically an intracellular pathway, which is activated or otherwise regulated by signaling from IGF1R, either directly or indirectly. Exemplary IGF1R signaling pathways are the PI3K-Akt-mTOR pathway and the Ras-Raf-MEK-ERK pathway. Constituents of an IGF1R signaling pathway include any molecules the expression of which is modulated as part of the signaling cascade of a pathway activated or otherwise regulated by IGF1R, and include molecules intermediate between IGF1R and downstream pathways, such as IRS-1, IRS-2 and PAK-1. The term IGF1R signaling pathway is readily understood by those skilled in the art (see for example, Chitnis et al., 2008).

As used herein the term "inhibitor" when used in the context of an IGF1R inhibitor or a BRAF inhibitor refers to any agent capable of inhibiting either or both the expression or activity of IGF1R or mutant BRAF, either directly or indirectly, or the expression or activity of one or more constituents of an IGF1R or BRAF—associated pathway, such as a signaling pathway. Such constituents may be molecules activated, inhibited or otherwise modulated prior to, in conjunction with, or as a consequence of IGF1R or mutant BRAF activity. Typically an IGF1R or BRAF—associated pathway is a downstream signaling pathway. The present invention contemplates inhibitors of constituents of IGF1R signaling pathways as this term is defined herein within the meaning of "IGF1R inhibitor". An inhibitor may operate to prevent transcription, translation, post-transcriptional or post-translational processing or otherwise inhibit the activity of IGF1R or BRAF or a constituent of an IGF1R or BRAF—associated pathway in any way, via either direct or indirect action. The inhibitor may for example be nucleic acid, peptide, any other suitable chemical compound or molecule or any combination of these. It will be understood that in indirectly impairing the activity of IGF1R or mutant BRAF or a constituent of an IGF1R or BRAF—associated pathway, the inhibitor may affect the activity of molecules which regulate, or are themselves subject to regulation or modulation by, the IGF1R or BRAF or component of an IGF1R or BRAF—associated pathway. Moreover, an "inhibitor" in the context of the present disclosure need not fully or completely inhibit the expression or activity of IGF1R or BRAF. Rather, the inhibition may be to an extent, and/or for a time, sufficient to produce the desired effect. As such inhibition may be in magnitude and/or be temporal in nature.

As used herein the term "BRAF inhibitor" refers to an inhibitor of a mutant BRAF protein.

As used herein the term "sensitivity" is used in its broadest context to refer to the ability of a cell to survive exposure to an agent designed to inhibit the growth of the cell, kill the cell or inhibit one or more cellular functions.

As used herein the term "resistance" is used in its broadest context to refer to the reduced effectiveness of a therapeutic agent (for example an IGF1R or BRAF inhibitor) to inhibit the growth of a cell, kill a cell or inhibit one or more cellular functions, and to the ability of a cell to survive exposure to an agent designed to inhibit the growth of the cell, kill the cell or inhibit one or more cellular functions. The resistance displayed by a cell may be acquired, for example by prior exposure to the agent, or may be inherent or innate. The resistance displayed by a cell may be complete in that the agent is rendered completely ineffective against the cell, or may be partial in that the effectiveness of the agent is reduced.

The term "subject" as used herein refers to mammals and includes humans, primates, livestock animals (e.g. sheep, pigs, cattle, horses, donkeys), laboratory test animals (e.g. mice, rabbits, rats, guinea pigs), performance and show animals (e.g. horses, livestock, dogs, cats), companion animals (e.g. dogs, cats) and captive wild animals. Preferably, the mammal is human or a laboratory test animal. Even more preferably, the mammal is a human.

Embodiments of the invention described herein employ, unless otherwise indicated, conventional molecular biology and pharmacology known to, and within the ordinary skill of, those skilled the art. Such techniques are described in, for example, "Molecular Cloning: A Laboratory Manual", $2^{nd}$ Ed., (ed. by Sambrook, Fritsch and Maniatis) (Cold Spring Harbor Laboratory Press: 1989); "Nucleic Acid Hybridization", (Hames & Higgins eds. 1984); Oligonucleotide Synthesis" (Gait ed, 1984); Remington's Pharmaceutical Sciences, $17^{th}$ Edition, Mack Publishing Company, Easton, Pa., USA.; "The Merck Index", $12^{th}$ Edition (1996), Therapeutic Category and Biological Activity Index,—and "Transcription & Translation", (Hames & Higgins eds. 1984).

As described and exemplified herein the inventors have identified therapeutic utilities for the miRNA miR-7-5p useful in the treatment of cancers and tumours expressing IGF1R or a constituent of an IGF1R signaling pathway, in particular melanoma. Disclosed herein is the ability of miR-7-5p to inhibit the expression in melanoma cells of molecules in the IGF1R downstream signaling pathways including insulin receptor substrate 2 (IRS-2), p21-activated kinase 1 (PAK1) and focal adhesion kinase (FAK), which in turn abolished downstream activity of Akt and ERK, and to reduce melanoma cell viability. miR-7-5p sensitizes melanoma cancer cells to, and acts synergistically with, a variety of therapeutic agents used to treat melanoma and against which resistance can develop, including BRAF inhibitors, IGF1R inhibitors and DNA alkylating chemotherapeutic agents. It has also been found that miR-7-5p inhibits the migration and invasion of melanoma cells indicating a role for miR-7-5p in the prevention or inhibition of melanoma metastasis.

In one aspect the invention described herein provides a synergistic composition for the treatment of a cancer or tumour expressing IGF1R or a constituent of an IGF1R signaling pathway, the composition comprising a miR-7-5p miRNA, a precursor or variant thereof or a miRNA comprising a seed region comprising the sequence GGAAGA, and at least one of a BRAF inhibitor, an IGF1R inhibitor and a DNA alkylating chemotherapeutic agent.

In another aspect the invention provides a method for treating a cancer or tumour expressing IGF1R or a constituent of an IGF1R signaling pathway in a subject, comprising administering to the subject synergistically effective amounts of a miR-7-5p miRNA, a precursor or variant thereof or a miRNA comprising a seed region comprising the sequence GGAAGA, and at least one therapeutic agent selected from of a BRAF inhibitor, an IGF1R inhibitor and a DNA alkylating chemotherapeutic agent.

In a further aspect the invention provides a method for sensitising a cancer or tumour cell expressing IGF1R or a constituent of an IGF1R signaling pathway to a therapeutic agent selected from BRAF inhibitor, an IGF1R inhibitor and a DNA alkylating chemotherapeutic agent, the method comprising contacting the cell with an effective amount of a miR-7-5p miRNA, a precursor or variant thereof or a miRNA comprising a seed region comprising the sequence GGAAGA.

In a further aspect the invention provides a method for inhibiting or preventing cancer metastasis or cancer cell migration, wherein the cancer expresses IGF1R or a constituent of an IGF1R signaling pathway, the method comprising administering to a subject in need thereof and effective amount of a miR-7-5p miRNA, a precursor or variant thereof or a miRNA comprising a seed region comprising the sequence GGAAGA.

In particular embodiments, the cancer is melanoma. The melanoma to be treated in accordance with the aspects and embodiments disclosed herein may be of any stage, including for example, melanoma in situ, invasive melanoma, metastatic melanoma and disseminated melanoma (stage IV metastatic melanoma). Similarly the melanoma may be of any type, including, for example, lentigomaligna, lentigomaligna melanoma, superficial spreading melanoma, acral-lentiginous melanoma, mucosal melanoma, nodular melanoma, polypoid melanoma, desmoplastic melanoma, amelanotic melanoma, and soft-tissue melanoma. In particular embodiments the melanoma is metastatic melanoma.

The melanoma may comprise cells that express a mutant BRAF, NRAS and/or PTEN. By way of example only, a number of BRAF mutations have been identified associated with melanoma, such mutations including R461I, I462S, G463E, G463V, G465A, G465E, G465V, G468A, G468E, N580S, E585K, D593V, F594L, G595R, L596V, T598I, V599D, V599E (now V600E), V599K, V599R, K600E, and A727V. The present disclosure contemplates the treatment of melanoma in which any of these mutations may be present, or in which other BRAF mutations, NRAS or PTEN mutations may be present.

Particular embodiments disclosed herein contemplate the sensitization of cancers and cells to, and the administration of, BRAF inhibitors, IGF1R inhibitors and DNA alkylating chemotherapeutic agents. Cancers and cancer cells may be sensitised to a variety of inhibitors and chemotherapeutic agents. For example, suitable IGF1R and BRAF inhibitors include any compounds capable of blocking, inhibiting or otherwise preventing IGF1R or BRAF from carrying out their biological functions in the cancer cells in which they are expressed. Typically the BRAF is a mutant BRAF and the BRAF inhibitor may be a mutant BRAF—specific inhibitor or mutant BRAF—selective inhibitor. The mutant BRAF may comprise the V600E mutation. Suitable inhibitors may be naturally occurring or naturally derived molecules or may be synthetically derived or produced, and may be, for example, small molecules, antibodies, such as monoclonal antibodies, and antisense nucleic acids. Suitable BRAF inhibitors include PLX4032 (RG7204; vemurafenib; such as Zelboraf®), PLX4720, GDC-0879, and sorafenib-tosylate (Bay 43-9006). In particular embodiments, the BRAF inhibitor is PLX4032. In particular embodiments, the IGF1R inhibitor is a tyrosine kinase inhibitor, and may be selected from picropodophyllin (PPP) and NVP-AEW541. In particular embodiments, the chemotherapeutic agent is temozolomide (TMZ; such as Temodar®). Other suitable BRAF inhibitors, IGF1R inhibitors and DNA alkylating agents will be known to those skilled in the art, and the skilled addressee will appreciate that the scope of the present disclosure is not limited by reference to the specific inhibitors or agents disclosed herein.

Cancers and cancer cells to which aspects and embodiments disclosed herein relate may be BRAF inhibitor-resistant or BRAF inhibitor-sensitive, or may be BRAF inhibitor-naïve (that is, cancers or cells that have not previously been exposed to a BRAF inhibitor). Similarly, cancers and cancer cells to which aspects and embodiments disclosed herein relate may be IGF1R inhibitor-resistant or IGF1R inhibitor-sensitive, or may be IGF1R inhibitor-naïve (that is, cancers or cells that have not previously been exposed to an IGF1R inhibitor). Similarly, cancers and cancer cells to which aspects and embodiments disclosed herein relate may be resistant or sensitive to DNA alkylating agents, or may not have been exposed to such agents.

Cancers and cells to which aspects and embodiments disclosed herein relate that are resistant to BRAF inhibitors, IGF1R inhibitors or DNA alkylating agents may be intrinsically resistant or may have acquired resistance. In the case of melanoma, the development of resistance to inhibitors of mutant BRAF is a particular and developing problem. It is also known that many melanomas acquire mutations in MEK, the molecule downstream of Raf in the Ras-Raf-MEK-ERK pathway, in particular melanomas that have acquired resistance to BRAF inhibitors. Accordingly embodiments of the present invention also contemplate the sensitisation of cancers and cells to MEK inhibitors. Several MEK inhibitors are currently in development, including, by way of non-limiting example, AZD6244 and ARRY-162.

Aspects and embodiments of the present invention provide for the administration of miRNAs. miRNAs bind the 3'-UTRs of target mRNAs and important in this binding is a so-called 'seed' region of approximately 6-7 nucleotides near the 5' end of the miRNA (typically nucleotide positions 2 to 8). Accordingly, embodiments of the present invention broadly contemplate contacting cells or tissue, or administering to subjects in need thereof, one or more miRNA, at least one of which comprises the seed region of miR-7-5p. In particular embodiments this seed region comprises the sequence GGAAGA (SEQ ID NO:5).

In particular embodiments, miR-7-5p is employed. The nucleotide sequence of mature human miR-7-5p (hsa-miR-7-5p) is provided in SEQ ID NO: 1. Additional sequence information for the miR-7-5p miRNA can be found at microrna.sanger.ac.uk/sequehces/index.shtml. Like most miRNAs, miR-7-5p is highly conserved between different species. Thus, whilst typically the miRNA may be derived from the species of the subject to be treated, or constitute a sequence identical to miRNA from that species, this need not be the case in view of, for example, the high level of sequence conservation of miRNA sequences between species.

Embodiments of the invention also contemplate the administration of miRNA variants of miR-7-5p. Variants include nucleotide sequences that are substantially similar to sequences of miRNA disclosed herein. Variants include nucleotide sequences that are substantially similar to sequences of miRNA disclosed herein. In some embodiments, the variant miRNA to be administered comprises a sequence displaying at least 80% sequence identity to the sequence of human miR-7-5p (SEQ ID NO:1). In some embodiments, the miRNA to be administered comprises a sequence displaying at least 90% sequence identity to SEQ ID NO:1. In other embodiments, the miRNA to be administered comprises a sequence displaying at least 91%, 92%, 93%, 94%, 95%, 96%, 97%, 98% or 99% sequence identity to SEQ ID NO:1. Alternatively or in addition variants may comprise modifications, such as non-natural residues at one or more positions with respect to the miR-7-5p sequence.

Also contemplated is the administration of a precursor molecule of miR-7-5p or of a miRNA comprising a seed region comprising the sequence GGAAGA. miRNAs are generated from RNA transcripts (pri-miRNAs) that usually contain several hundred nucleotides transcribed from regions of non-coding DNA. Pri-miRNAs are processed in the nucleus by RNase III endonuclease to form stem-loop precursors (pre-miRNAs) of approximately 70 nucleotides. Pre-miRNAs are actively transported into the cytoplasm where they are further processed into short RNA duplexes, typically of 21-23 nucleotides, one of which represents the functional miRNA strand. The administration of such pri-miRNA and pre-miRNA precursors is contemplated herein, wherein the pri-miRNA or pre-miRNA is cleaved and intracellularised to generate a functional miRNA. Exemplary precursors of hsa-miR-7-5p contemplated by the present invention include, but are not limited to hsa-miR-7-5p-1, hsa-miR-7-5p-2 or hsa-miR-7-5p-3, as set forth in SEQ ID NOs:2 to 4, respectively.

In addition to the full-length miR-7-5p molecule, such as that shown in SEQ ID NO:1, the term "miR-7-5p" also includes fragments of a miR-7-5p molecule provided the fragments are functional fragments. The term "fragment" of a miRNA molecule means a portion of the full-length molecule. The size of the fragment is limited only in that it must be a functional fragment, that is, able to modulate the expression of IGF1R or components of IGF1R signaling pathways and have therapeutic utility against IGF1R expressing cancer cells as described herein. Typically, the fragment will comprise at least the seed region sequence GGAAGA (SEQ ID NO: 5).

Administration of the miRNA may be directly to a subject in need of treatment, or may be ex vivo administration to cells or tissue derived from a subject. The miRNA to be administered may be synthetically produced or naturally derived from a cellular source.

Also contemplated by embodiments of the invention is the administration of agents capable of stimulating or enhancing the expression or activity of miRNA described herein. Such agents may be proteinaceous, non-proteinaceous or nucleic acid-based and include, for example, molecules and compounds capable of binding to the regulatory sequences of miRNA genes to thereby induce or enhance the level of endogenous expression of the miRNA. Those skilled in the art will appreciate that the scope of the invention is not so limited and any agents capable of stimulating or enhancing miRNA expression or activity are contemplated and fall within the scope of the present disclosure.

Also contemplated by embodiments of the invention is the administration of a miRNA linked to an additional agent capable of delivering the miRNA to the desired site. In some embodiments the link between the miRNA and the additional agent is a cleavable link. The presence of a cleavable link allows for cleavage of the miRNA from the additional agent, for example after internalisation into cells expressing IGF1R.

Contacting a cell or cancer with a miRNA or agent capable of stimulating or enhancing the expression or activity of a miR-7-5p miRNA may be achieved by any method known in the art. In some embodiments contacting the cell and the miRNA occurs in vivo. The miRNA or agent capable of stimulating or enhancing the expression or activity of a miR-7-5p miRNA may be contacted with the cell directly, i.e. applied directly to a cell requiring sensitizing to a therapeutic agent, or alternatively may be combined with the cell indirectly, e.g. by injecting the molecule into the bloodstream of a subject, which then carries the molecule to the cell requiring sensitizing to a therapeutic agent. Further, a sample may be removed from a subject and combined with an miRNA or agent capable of stimulating or enhancing the expression or activity of a miR-7-5p miRNA in vitro prior to returning at least a portion of the sample back to the subject. For example, the sample may be a blood sample which is removed from a subject and combined with the miRNA prior to injecting at least a portion of the blood back into the subject.

Embodiments of the present invention also provide methods for determining a change in sensitivity of a cancer or cancer cell expressing IGF1R or a constituent of an IGF1R signaling pathway to an IGF1R inhibitor, a BRAF inhibitor or a DNA alkylating chemotherapeutic agent. Such methods may comprise
 (a) administering to a subject a miR-7-5p miRNA, a precursor or variant thereof, or a miRNA comprising a seed region comprising the sequence GGAAGA;
 (b) determining the sensitivity or resistance to the IGF1R inhibitor, BRAF inhibitor or DNA alkylating chemotherapeutic agent in a biological sample from the subject;
 (c) repeating steps (a) and (b) at least once over a period of time; and
 (d) comparing said sensitivity or resistance in the samples.

Embodiments of the present invention also provide methods for evaluating the efficacy of a treatment regime in a subject suffering from cancer, wherein the cancerous cells express IGF1R or a constituent of an IGF1R signaling pathway. Such methods may comprise:
 (a) treating the subject with a combination of (i) an IGF1R inhibitor, a BRAF inhibitor or a DNA alkylating chemotherapeutic agent and (ii) a miR-7-5p miRNA, a precursor or variant thereof, or a miRNA comprising a seed region comprising the sequence GGAAGA for a period sufficient to evaluate the efficacy of the regime;
 (b) obtaining a biological sample from the subject;
 (c) determining the sensitivity or resistance to the IGF1R inhibitor, B-RAF inhibitor or DNA alkylating chemotherapeutic agent in the sample;
 (d) repeating steps (b) and (c) at least once over a period of time of the treatment; and
 (e) determining whether said sensitivity or resistance changes over the period of time,
 wherein a change in the sensitivity or resistance is indicative of the efficacy of the treatment regime.

miRNA, IGF1R inhibitors, BRAF inhibitors and chemotherapeutic agents inhibitors may be administered to subjects, or contacted with cells, in accordance with aspects and embodiments of the present invention in the form of pharmaceutical compositions, which compositions may comprise one or more pharmaceutically acceptable carriers, excipients or diluents suitable for in vivo administration to subjects. Where multiple agents are to be administered, for example in synergistic combinations as disclosed herein, each agent in the combination may be formulated into separate compositions or may be co-formulated into a single composition. If formulated in different compositions the compositions may be co-administered. By "co-administered" is meant simultaneous administration in the same formulation or in two different formulations via the same or different routes or sequential administration by the same or different routes. By "sequential" administration is meant a time difference of from seconds, minutes, hours or days between the administration of the two compositions. The compositions may be administered in any order, although in particular embodiments it may be advantageous for the miRNA to be administered prior to the IGF1R inhibitor, BRAF inhibitor or DNA alkylating chemotherapeutic agent.

Compositions may be administered to subjects in need thereof via any convenient or suitable route such as by topical (including dermal, transdermal, subcutaneous, etc), parenteral (including, for example, intraarterial, intravenous, intramuscular, subcutaneous), oral, nasal, mucosal (including sublingual), or intracavitary routes. Thus compositions may be formulated in a variety of forms including solutions, suspensions, emulsions, and solid forms and are typically formulated so as to be suitable for the chosen route of administration, for example as capsules, tablets, caplets, elixirs for oral ingestion, in an aerosol form suitable for administration by inhalation (such as by intranasal inhalation or oral inhalation), ointment, cream, gel, jelly or lotion suitable for topical administration, or in an injectable formulation suitable for parenteral administration. The preferred route of administration will depend on a number of factors including the condition to be treated and the desired outcome.

The most advantageous route for any given circumstance can be determined by those skilled in the art. For example, in circumstances where it is required that appropriate concentrations of the desired agent are delivered directly to the site in the body to be treated, administration may be regional rather than systemic. Regional administration provides the capability of delivering very high local concentrations of the desired agent to the required site and thus is suitable for achieving the desired therapeutic or preventative effect whilst avoiding exposure of other organs of the body to the compound and thereby potentially reducing side effects.

For the treatment of melanoma, topical administration may in many cases be a suitable and convenient route of administration.

In general, suitable compositions may be prepared according to methods known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Compositions suitable for topical administration may be in any suitable form, formulated for example as liniments, lotions, creams, gels, ointments or pastes. Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenylpolysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

Compositions may also be impregnated into transdermal patches, plasters, and wound dressings such as bandages or hydrocolloid dressings, preferably in liquid or semi-liquid form.

For administration as an injectable solution or suspension, non-toxic parenteral acceptable diluents or carriers can include Ringer's solution, medium chain triglyceride (MCT), isotonic saline, phosphate buffered saline, ethanol and 1,2 propylene glycol. Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propylparaben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate. polyoxyethylenesorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Methods for preparing parenteral administrable compositions are apparent to those skilled in the art, and are described in more detail in, for example, Remington's Pharmaceutical Science, 15th ed., Mack Publishing Company, Easton, Pa., hereby incorporated by reference herein. The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silica ceoussilicas, and other ingredients such as lanolin, may also be included.

Methods and pharmaceutical carriers for preparation of pharmaceutical compositions are well known in the art, as set out in textbooks such as Remington's Pharmaceutical Sciences, $20^{th}$ Edition, Williams & Wilkins, Pennsylvania, USA. The carrier will depend on the route of administration, and again the person skilled in the art will readily be able to determine the most suitable formulation for each particular case.

The compositions may also be administered in the form of liposomes. Liposomes are generally, derived from phospholipids or other lipid substances, and are formed by mono- or multilamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidylcholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

The following examples are illustrative of the invention and should not be construed as limiting in any way the general nature of the disclosure of the description throughout this specification.

General Methods

Chemicals and Reagents

NVP-AEW541 (Cayman Chemical, Ann Arbor, Mich.) and picropodophyllin (PPP; Santa Cruz Biotechnology, Santa Cruz, Calif.) were prepared as a 10 mM stock solution in dimethyl sulfoxide (DMSO) (Sigma-Aldrich; Sydney, Australia). Temozolomide (TMZ; Sigma-Aldrich) and PLX4032 (Selleck Chemicals, Houston, Tex.) were prepared as 50 mM and 100 mM stock solutions, respectively in DMSO. For experimental purposes the drugs were diluted in fresh media before addition to cell cultures. Synthetic miRNA precursor molecules corresponding to human miR-7-5p (Pre-miR miRNA Precursor Product ID: PM10047) (Ambion; Victoria, Australia) and a negative control miRNA (miR-NC; Pre-miR miRNA Precursor Negative Control #1, Product ID: AMI7110) (Ambion) were prepared as 50 µM stock solutions in RNase-free water (Ambion). In experiments testing the effects of miR-7-5p and/or drug, vehicle control cell cultures were treated with an equivalent v/v dilution of DMSO (in place of drug) or Lipofectamine 2000 (Invitrogen; Victoria, Australia) (in place of miR-7-5p and miR-NC).

Cell Lines and Cell Culture

WM266-4, A375 and SK-MEL-28 melanoma cells were obtained from the American Type Culture Collection (ATCC). MM96L and A2058 melanoma cells were a kind gift from Prof Peter Klinken, Western Australian Institute for Medical Research (WAIMR). WM266-4, SK-MEL-28, MM96L and A2058 cells were cultured at 37° C. in 5% $CO_2$ with RPMI 1640 media supplemented with 10% foetal bovine serum (FBS). An IGF1R inhibitor-sensitive breast cancer cell line (MCF-7) was obtained from ATCC and were cultured at 37° C. in 5% $CO_2$ with RPMI 1640 media supplemented with 10% FBS. BRAF inhibitor-resistant melanoma cells A375 and WM266-4, stably expressing a Q61 NRAS mutant gene, were a kind gift from Assoc. Prof. Grant McArthur at the Peter MacCallum Cancer Centre. 1205Lu melanoma cells were a kind gift from Assoc. Prof Nikolas Haas at the University of Queensland Diamantina Institute.

Drug Sensitivity Assays

Cells were seeded in 96-well plates at a density of $2.5 \times 10^3$ cells per well and after overnight incubation, treated with drug at a range of concentrations. Cell viability was measured after 4 days using a CellTitre 96 Aqueous One Solution Cell Proliferation Assay Kit (Promega; Sydney, Australia) as per manufacturer's instructions and a FLUOstar OPTIMA microplate reader (BMG Labtech; Victoria, Australia).

miRNA Precursor and siRNA Transfections

Optimal cell numbers were transfected using Lipofectamine 2000 (Invitrogen) with miR-7-5p (SEQ ID NO: 1; synthesised by Ambion) or miR-NC precursor molecules (hereinafter "miR-NC"; Ambion AM17110) at final concentrations ranging from 1-30 nM. For siRNA transfections, Silencer Select siRNAs (Invitrogen) Negative Control No. 1 (si-NC; 4390843), si-IRS-2 #1 (s16486), si-IRS-2 #2 (s16487) were transfected using Lipofectamine 2000 (Invitrogen) according to the manufacturer's protocol. Cells were harvested 24 hours later for RNA or 2-3 days after transfection for protein extraction.

Protein Extraction

Protein was harvested with Cytoplasmic Extract Buffer (CEB)-containing PhosSTOP phosphatase inhibitors (Roche; New South Wales, Australia) and Complete EDTA-free protease inhibitors (Roche). Cell lysates were frozen at −80° C. overnight, cleared by centrifugation at 13,000×g for 5 min, and supernatants collected. Total protein concentrations were determined by Bio-Rad protein assay (Bio-Rad;

New South Wales, Australia) as per manufacturer's instructions and using a FLUOstar OPTIMA microplate reader.

Western Blotting

Fifteen μg of total protein samples were resolved on NuPAGE NO VEX 4-12% Bis-Tris gels (Invitrogen) and transferred to polyvinylidene fluoride (PVDF) western blotting membranes (Roche). The blots were blocked for 1 hour with Odyssey Blocking Buffer (Millennium Science, Victoria, Australia) and incubated overnight at 4° C. with anti-IGF1R, anti-phospho-IGF1R, anti-IRS-1, anti-IRS-2, anti-phospo-IRS-2, anti-ERK 1/2, anti-phospho-ERK 1/2, anti-Akt, anti-phospho-Akt (Ser-473), anti-PAK1 (all from Cell Signaling Technology, Beverly, Mass.), or anti-FAK (Santa Cruz Biotechnology), anti-phospho-IRS-2 (Ser-731; Abcam, Cambridge, Mass.), or anti-β-actin (Abcam), followed by incubation with infrared-conjugated secondary antibodies for 1 hour at room temperature. The membranes were scanned with an Odyssey SA scanner to visualize protein expression (LICOR Biosciences, Lincoln, Nebr.).

Cell Viability Assays

Cells were seeded in 96-well plates at a density of $2.5 \times 10^3$ cells per well and transfected with miRNA precursor molecules as above. Cell viability was measured 5 days after transfection using CellTitre 96 Aqueous One Solution Cell Proliferation Assay Kit (MTS assay) and a FLUOstar OPTIMA microplate reader. For synergy analysis between drugs and miR-7-5p, cells were plated as above and drug or DMSO was added 3 days after transfection with miR-7-5p or miR-NC for 4 days, at which time cell viability was measured (7 days after transfection).

Cell Migration and Invasion Assays

Cell migration and invasion was monitored with a Real-Time Cell Analyser dual-plate (RTCA DP) xCELLigence System (Roche Applied Science; Mannheim, Germany). This instrument employs cellular migration plates (CIM-plate 16) which contain microelectronic sensors on the underside of an 8 μm microporous polyethylene terephthalate (PET) membrane of a Boyden-like upper chamber and a lower chamber containing media or chemoattractant. As cells migrate or invade from the upper chamber to the lower chamber they interact with the sensors causing an increase in electrical impedance. Changes in cell impedance over time relates to a change in the number of cells interacting with the sensors, allowing real-time measurement of cell migration as a cell index value. For migration assays, cells were seeded in 6-well plates at a density of $5 \times 10^5$ cells per well and transfected with miRNA precursor molecules as above at a final concentration of 30 nM. After 48 h incubation cells were trypsinised, resuspended in serum free media and seeded into the upper chamber of CIM-plates. The lower chambers were filled with media containing 10% FBS (chemoattractant) or serum free media as a control. Migration was monitored over a 24 hour period with impedance measurements every 15 min. For invasion assays, the CIM-plates were coated with Matrigel (BD Biosciences; diluted at a ratio of 1:20 in serum free medium) approximately 4 hours prior to seeding cells.

Statistics

All results are presented as means±standard deviation (S.D.). Statistical significance was calculated using Student's t test (one-tailed, unpaired) and the level of significance was set at $p<0.05$. Drug sensitivity ($IC_{50}$) was calculated using GraphPad Software (GraphPad Prism, version 5.04). The Bliss additivism model was used for synergy analysis. Calculations are made using the formula: $E_{bliss} = (E_A + E_B) - (E_A \times E_B)$, where $E_A$ and $E_B$ are the fractional inhibitions obtained by drug A (miR-7-5p) alone and drug B (temozolomide, PLX4032, PPP or NVP-AEW541) alone at specific concentrations. Here, $E_{bliss}$ is the fractional inhibition expected if the combination of miR-7-5p and drug B was exactly additive. If the experimentally measured fractional inhibition is greater than $E_{bliss}$, the combination is synergistic.

Example 1—miR-7-5p Reduces Expression of Molecules of the IGF1R Pathway and Abrogates Activation of the Akt and ERK Signaling A panel of four metastatic melanoma cell lines was used in this study (SK-MEL-28, WM266-4, MM96L and A2058), with three harbouring V600E BRAF mutations, one with V600D BRAF mutation, two with PTEN mutations and two with p53 mutations, encompassing a broad spectrum of mutations important in the context of melanoma. These cell lines were transiently transfected with miR-NC or miR-7-5p precursor molecules at 15 nM final concentration. After 3 days incubation protein samples were harvested and resolved by SDS-PAGE, followed by immunoblotting for IGF1R, P-IGF1R, IRS-1, IRS-2, P-IRS-2, Akt, P-Akt, PAK1, ERK 1/2, P-ERK 1/2 and β-Actin (loading control). Comparisons between the miR-NC lane of the four cell lines (FIG. 1) show expression and activation of IGF1R signaling molecules varied for each of the cell lines, reflecting their different mutational characteristics. IGF1R and P-IGF1R were detected in SK-MEL-28, MM96L and A2058 cells. IRS-1 was detected at low levels across the cell lines, with MM96L having the highest expression. MM96L and A2058 cells had the highest expression of IRS-2; though P-IRS-2 was detected in all cell lines. PAK1, Akt and ERK 1/2 were detected at high levels across all cell lines. P-Akt was highest in the PTEN mutant cell lines WM266-4 and A2058 and P-ERK 1/2 was high across cell lines consistent with constitutive activation of the ERK pathway due to their BRAF mutant status.

Next the ability of miR-7-5p to reduce expression of IGF1R signaling pathway molecules was assessed. As illustrated in FIG. 1, when each of the cell lines were transfected with miR-7-5p, reductions in the protein level of PAK1 was consistently observed. No change in IGF1R expression was detected. IGF1R phosphorylation did not change for SK-MEL-28, increased in MM96L and decreased in A2058. IRS-1 expression varied across cell lines when transfected with miR-7-5p resulting in a modest increase in SK-MEL-28 and WM266-4 and decrease in A2058 transfected with miR-7-5p. IRS-2 expression and phosphorylation was reduced in A2058 and SK-MEL-28, respectively. Importantly, P-Akt (SK-MEL-28, WM266-4 and MM96L) and P-ERK 1/2 (A2058) were downregulated with miR-7-5p transfection, confirming the ability of miR-7-5p to regulate these critical downstream signaling pathways.

Example 2—miR-7-5p Reduces Viability of Melanoma Cells

Figure 2:
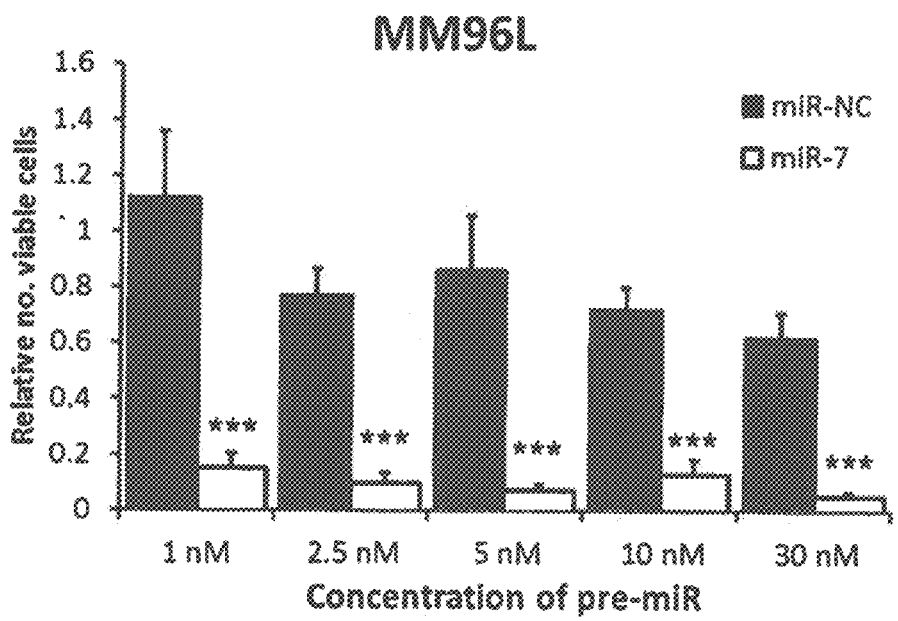
FIG. 2. miR-7-5p reduces melanoma cell viability. A. Cell titre analysis of MM96L cell viability 5 days post-transfection with miR-NC or miR-7-5p precursors at indicated concentration. B. A2058 cells were transfected and analysed for cell viability as in A. Data has been normalised to Lipofectamine 2000 (vehicle) only and is representative of three independent experiments. Bars represent S.D.,  indicates a significant difference from miR-NC ($p<0.01$), and * indicates significant difference from miR-NC ($p<0.001$).
Figure 2:
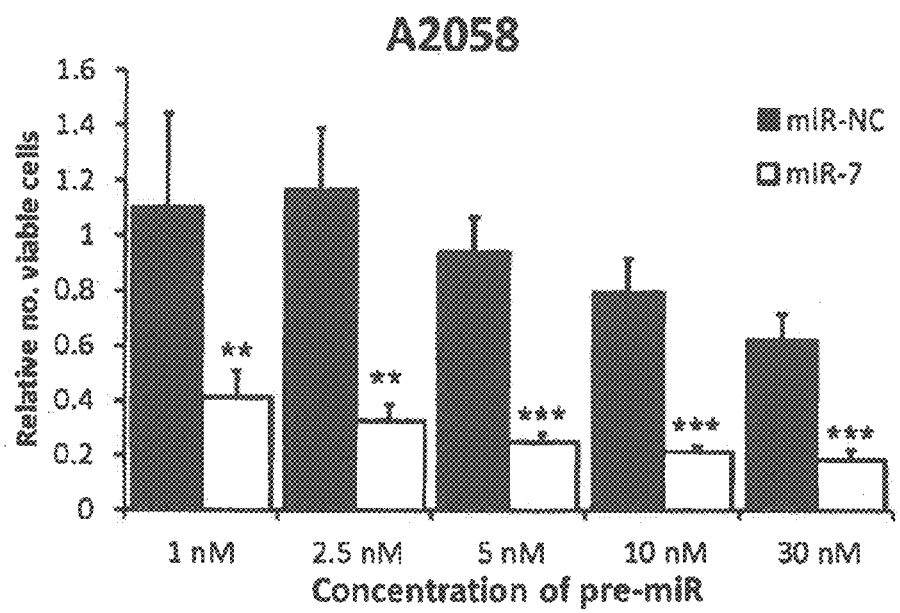

The negative regulation of Akt and ERK 1/2 activity in melanoma cells by miR-7-5p suggests delivering miR-7-5p might have therapeutic utility in this disease. To evaluate this, melanoma cell lines were transfected with miR-7-5p or miR-NC, and the effect on cell growth assessed by MTS assay. Comparing miR-NC and miR-7-5p transfected cells revealed that miR-7-5p significantly reduced cell viability in MM96L, A2058 (FIG. 2), SK-MEL-28 and WM266-4 cells (data not shown). Viability was significantly reduced at a final miR-7-5p concentration of 1 nM, suggesting that a small increase in miR-7-5p can have a significant impact on melanoma cell viability.

Example 3—miR-7-5p Sensitises Melanoma Cell Lines to NVP-AEW541 and Other Therapies To further evaluate the therapeutic utility of miR-7-5p in melanoma, its ability to synergise with various therapies was evaluated. Initially, the sensitivity of various melanoma cell lines was established for four different treatments: the IGF1R kinase inhibitors NVP-AEW541 and picropodophyllin (PPP), the BRAF mutant inhibitor PLX4032, and the DNA alkylating chemotherapeutic agent temozolomide (TMZ).

Figure 3:
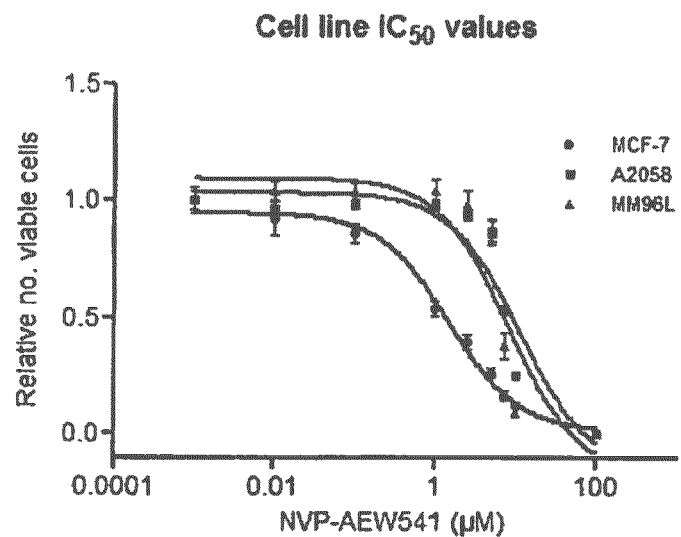
FIG. 3. Melanoma cell lines are resistant to IGF1R kinase inhibitor NVP-AEW541 and miR-7-5p can sensitise melanoma cell lines to a BRAF inhibitor, IGF1R inhibitors and a DNA alkylating chemotherapeutic agent. A. A2058, MM96L and MCF-7 (positive control) were treated with NVP-AEW541 over a range of concentrations (0.001-100 μM) and analysed for cell viability after 4 days. Data has been normalised to lowest concentration of drug. Bars represent mean difference in cell viability±S.D. Data representative of three independent experiments. B-E. A2058 cells were transfected with miR-NC or miR-7-5p precursors at 5 nM and treated with indicated drug (B, 5 μM NVP-AEW541; C, 100 nM PLX4032; D, 100 nM PPP; E, 150 μM TMZ) or DMSO 3 days post-transfection. Data represents cell viability 4 days after addition of drug or DMSO (7 days post-transfection). Data has been normalised miR-NC with DMSO and is representative of at least two independent experiments. Bars represent S.D., *** indicates significant difference from miR-NC ($p<0.001$), † indicates synergy between miR-7-5p and indicated drug treatment.
Figure 3:
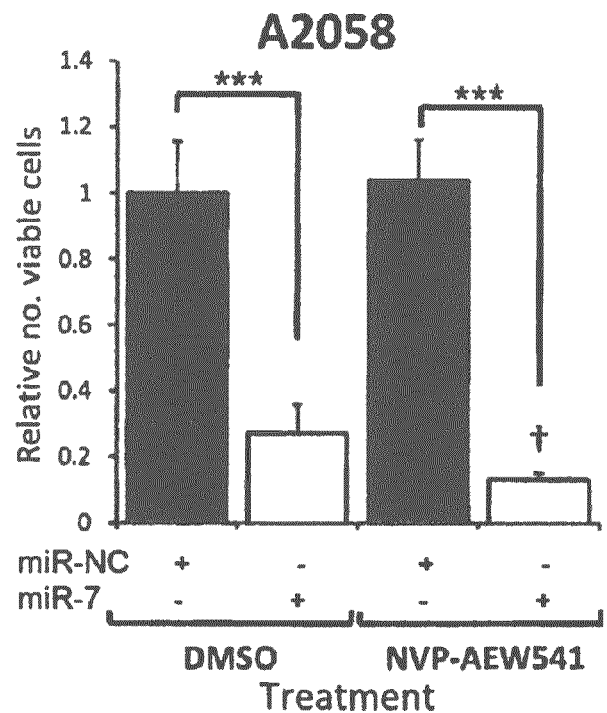
Figure 3:
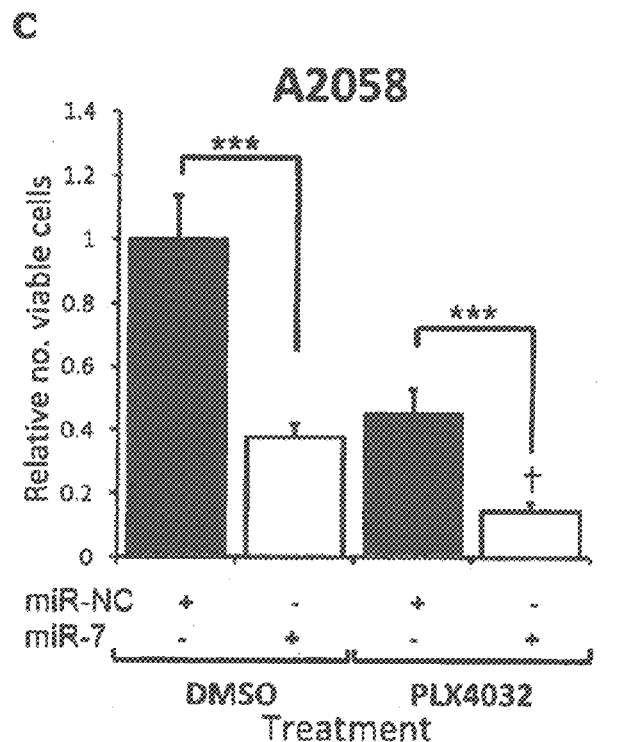
Figure 3:
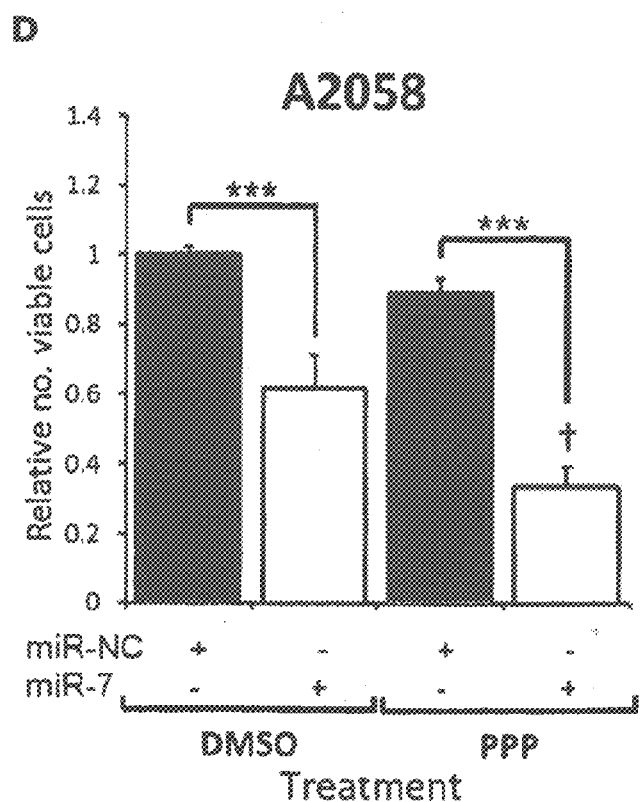
Figure 3:
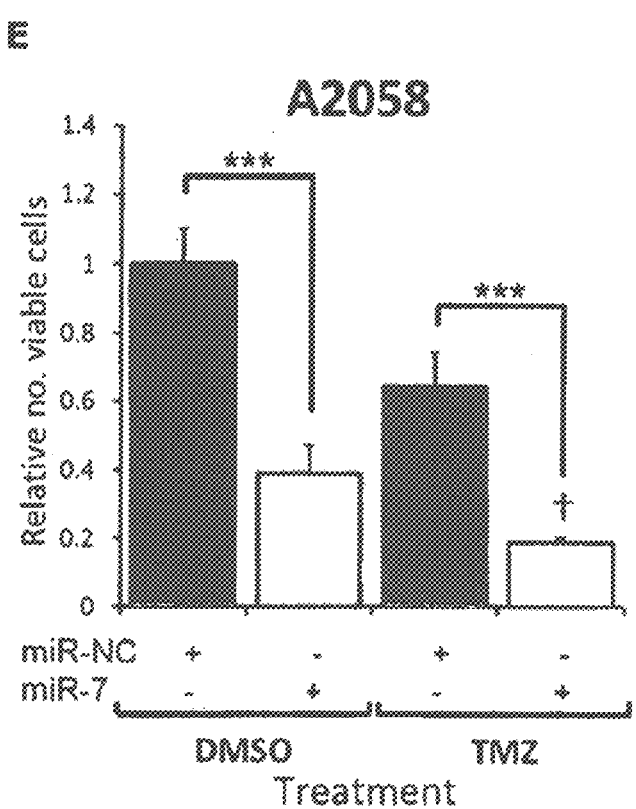

Consistent with the literature cell lines harbouring p53 mutations were highly resistant to TMZ treatment and therefore accurate $IC_{50}$ values could not be determined, while for the wild type p53 cell lines $IC_{50}$ values were 73.09 μM and 167.3 μM for WM266-4 and A2058, respectively. Several melanoma cell lines are reported to be sensitive to the IGF1R kinase inhibitor PPP. Consistent with this, the melanoma cell lines used herein were sensitive to the inhibitor with $IC_{50}$ values of 0.15-0.3 μM. Interestingly, melanoma cell lines were resistant to the IGF1R kinase inhibitor NVP-AEW541 ($IC_{50}$ values 8.27-25.05 μM) compared to a breast cancer cell line MCF-7 ($IC_{50}$=1.5 μM) reported to be sensitive to this drug and hence included as a positive control (FIG. 3A). The difference in sensitivity may be due to high levels of IRS-1 in MCF-7, which is reported as a determinant for sensitivity to NVP-AEW541, whereas, by comparison, melanoma cell lines have low expression of IRS-1 and high expression of IRS-2 (data not shown). It was also observed that in MCF-7 breast cancer cells, NVP-AEW541 treatment attenuated IGF-1-induced activation of Akt and ERK 1/2 signaling pathways, whereas in melanoma cell lines only Akt activity was abrogated (data not shown). This persistence of ERK 1/2 activity despite IGF1R inhibition may be related to the presence of activating BRAF mutations in the melanoma cell lines. All melanoma cell lines were highly sensitive to PLX4032, a result that was consistent with the literature, with $IC_{50}$ values of 0.08-0.23 μM.

Next the cells were transfected with miR-NC or miR-7-5p and after 3 days were treated with a suboptimal dose (below the $IC_{50}$) of NVP-AEW541, PPP, PLX4032, TMZ or DMSO (vehicle), and incubated for a further 4 days before assessing the effect on cell viability by MTS assay. The combination of miR-7-5p and treatment with NVP-AEW541, PPP, PLX4032 or TMZ resulted in a significant reduction in cell viability compared to miR-NC in A2058 cells (FIG. 3B). For each drug, the Bliss additivism model indicated that the observed fractional inhibition was greater than the calculated additive inhibition and therefore these combinations were synergistic. The analysis of synergy was extended into other melanoma cell lines and the results are shown in Table 1. These result's demonstrate that miR-7-5p can augment the activity of existing chemotherapeutics.

TABLE 1

Figure 4:
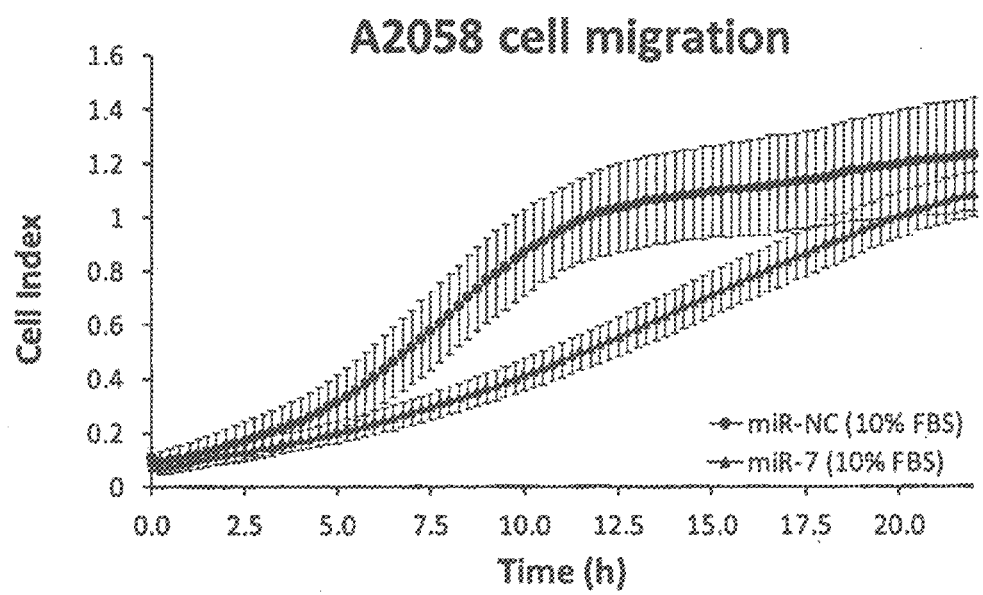
FIG. 4. miR-7-5p inhibits melanoma cell migration and blocks expression of several pro-migratory molecules. A. A2058 cells were transfected with miR-NC or miR-7-5p precursors at 30 nM and after 48 hours were seeded into CIM-plate 16 and migration monitored for 24 hours with an xCELLigence RTCA DP instrument. Data represents mean cell index±S.D. Data is representative of three independent experiments. B. WM266-4 and A2058 cells were transfected as in A. and protein harvested at the same time point for migration assay. Changes in protein expression were detected by immunoblot for FAK, IRS-2 and PAK1. β-Actin, loading control. Data is representative of three independent experiments.
Figure 4:
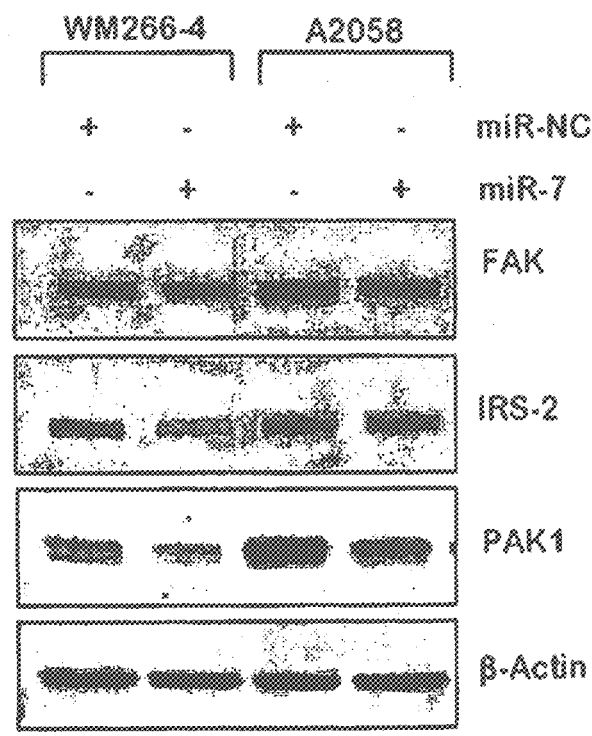

| Drug | Cell line | [miR-7-5p] | [drug] | $E_{Bliss}$ | $E_{Obs}$ | $E_{Obs}/E_{Bliss}$ |
|---|---|---|---|---|---|---|
| NVP-AEW541 | SK-MEL-28 | 5 nM | 5 μM | 0.474 | 0.588 | 1.24 |
| | | 5 nM | 5 μM | 0.265 | 0.309 | 1.17 |
| | WM266-4 | 5 nM | 5 μM | 0.715 | 0.757 | 1.06 |
| | MM96L | 5 nM | 5 μM | 0.515 | 0.547 | 1.06 |
| | A2058 | 5 nM | 5 μM | 0.720 | 0.866 | 1.20 |
| | | 5 nM | 5 μM | 0.769 | 0.846 | 1.10 |
| PPP | SK-MEL-28 | 5 nM | 100 nM | 0.292 | 0.526 | 1.80 |
| | | 5 nM | 100 nM | 0.391 | 0.508 | 1.30 |
| | A2058 | 5 nM | 100 nM | 0.447 | 0.663 | 1.48 |
| | | 5 nM | 100 nM | 0.684 | 0.704 | 1.03 |
| | | 5 nM | 100 nM | 0.420 | 0.496 | 1.18 |
| PLX4032 | SK-MEL-28 | 5 nM | 100 nM | 0.709 | 0.773 | 1.09 |
| | | 5 nM | 50 nM | 0.561 | 0.661 | 1.18 |
| | MM96L | 2.5 nM | 50 nM | 0.946 | 0.972 | 1.03 |
| | | 2.5 nM | 50 nM | 0.701 | 0.803 | 1.15 |
| | | 2.5 nM | 50 nM | 0.424 | 0.547 | 1.29 |
| | A2058 | 5 nM | 100 nM | 0.830 | 0.855 | 1.03 |
| | | 5 nM | 100 nM | 0.504 | 0.853 | 1.69 |
| | | 5 nM | 100 nM | 0.643 | 0.790 | 1.23 |
| TMZ | WM266-4 | 5 nM | 50 μM | 0.603 | 0.748 | 1.24 |
| | | 5 nM | 50 μM | 0.703 | 0.748 | 1.06 |
| | | 5 nM | 50 μM | 0.612 | 0.732 | 1.20 |
| | MM96L | 5 nM | 500 μM | 0.843 | 0.864 | 1.02 |
| | | 5 nM | 500 μM | 0.860 | 0.878 | 1.02 |
| | | 5 nM | 150 μM | 0.716 | 0.747 | 1.04 |
| | A2058 | 5 nM | 150 μM | 0.749 | 0.811 | 1.08 |
| | | 5 nM | 150 μM | 0.605 | 0.633 | 1.05 |
| | | 5 nM | 50 μM | 0.500 | 0.680 | 1.36 |

Where $E_{Obs}/E_{Bliss}$ is >1 the combination of treatment with miR-7-5p was said to be synergistic Example 4—miR-7-5p Inhibits Melanoma Cell Migration and Blocks Expression of Several Pro-Migratory Molecules To assess the effect of miR-7-5p overexpression on melanoma cell migration, WM266-4 and A2058 melanoma cells were transfected with miR-NC or miR-7-5p precursors, and after 48 hours cells were harvested and seeded into CIM-plates for monitoring of cell migration over a 24 hour period. miR-7-5p significantly inhibited migration of the A2058 and WM266-4 cells (FIG. 4A and data not shown).

To validate whether the effect of miR-7-5p on migration may be due to its downregulation of FAK, IRS-2, and/or PAK1, the expression of these molecules was evaluated in each of the cell lines simultaneously used for migration assays (FIG. 4B). Western blotting indicated a reduction in FAK, IRS-2 and PAK1 expression in both WM266-4 and A2058 cells that were transfected with miR-7-5p, suggesting a potential inhibitory role for miR-7-5p in melanoma cell migration and invasion, mediated at least in part via these miR-7-5p target molecules.

Figure 5:
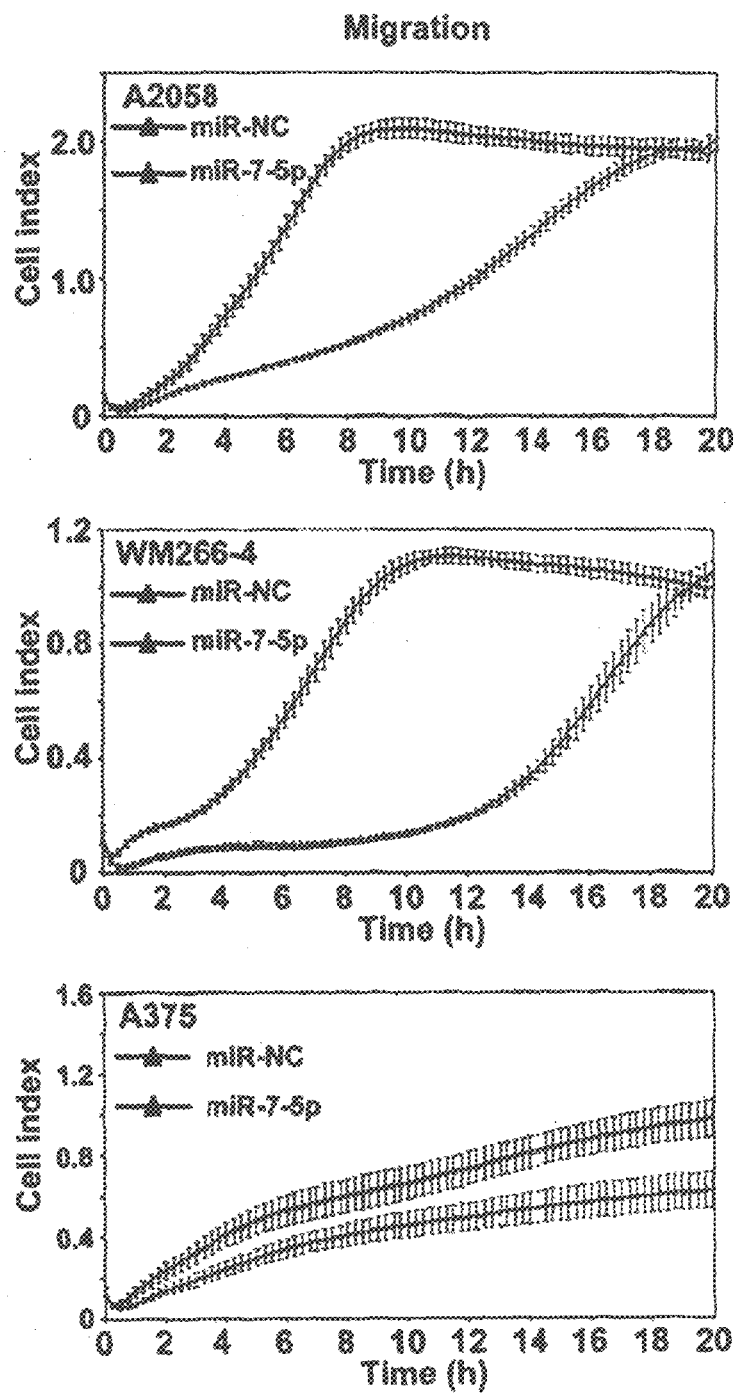
FIG. 5. miR-7-5p inhibits A2058, WM266-4 and A375 melanoma cell migration. Real time xCELLigence analysis of migration (represented by cell index) of A2058, WM266-4 and A375 melanoma cell lines following transfection with miR-7-5p or miR-NC.
Figure 6:
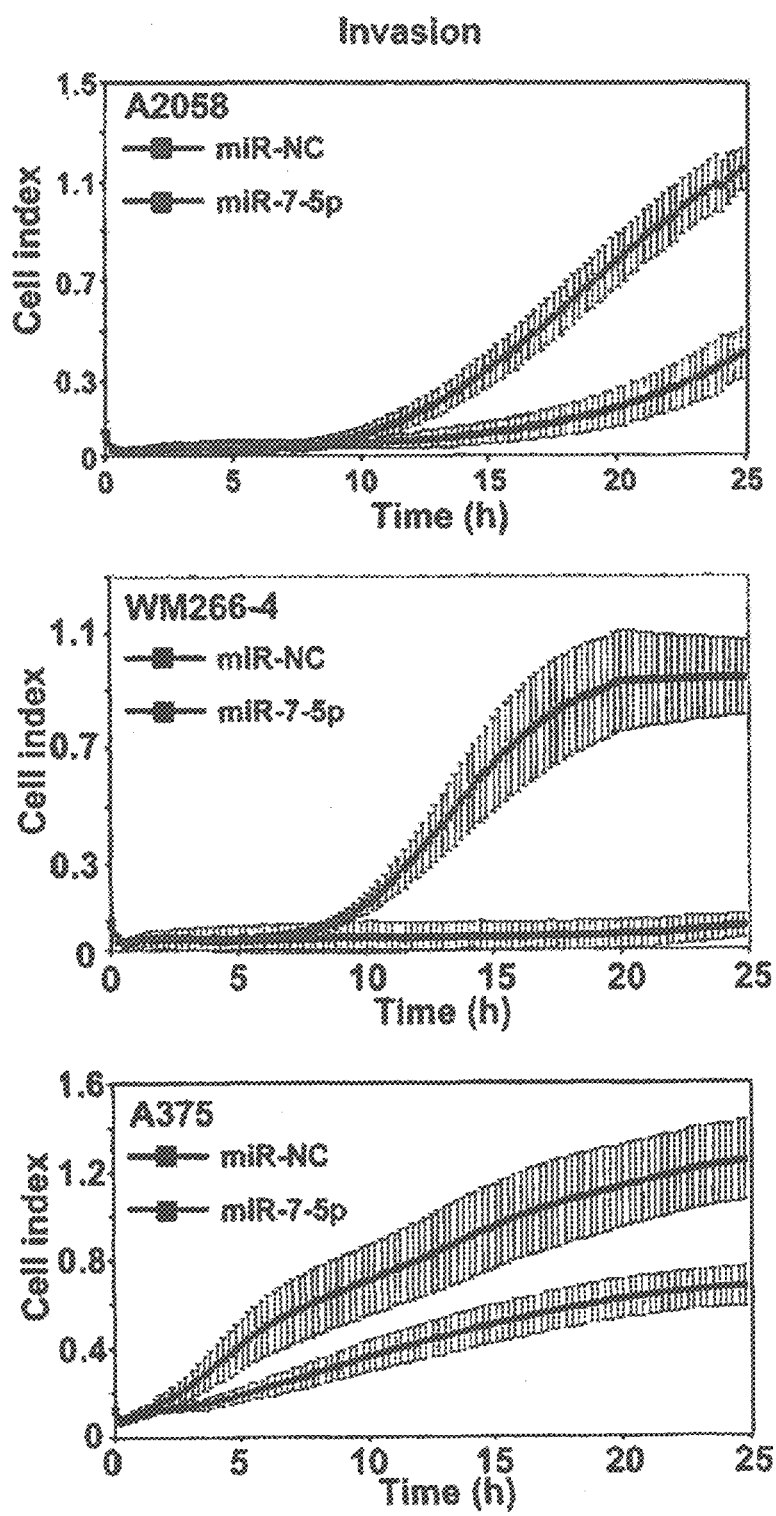
FIG. 6. miR-7-5p inhibits A2058, WM266-4 and A375 melanoma cell invasion. Real time xCELLigence analysis of invasion (represented by cell index) of A2058, WM266-4 and A375 melanoma cell lines following transfection with miR-7-5p or miR-NC.
Figure 7:
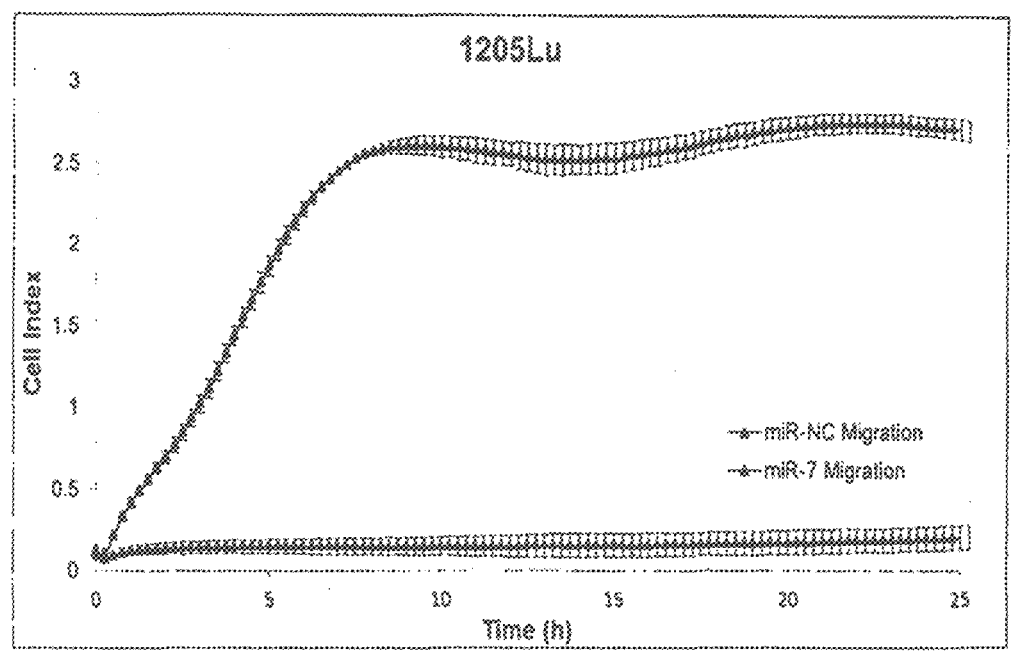
FIG. 7. miR-7-5p inhibits 1205Lu melanoma cell migration and invasion. A. Real time xCELLigence analysis of migration (represented by cell index) of 1205Lu melanoma cell lines following transfection with miR-7-5p or miR-NC. B. Real time xCELLigence analysis of invasion (represented by cell index) of 1205Lu melanoma cell lines following transfection with miR-7-5p or miR-NC.
Figure 7:
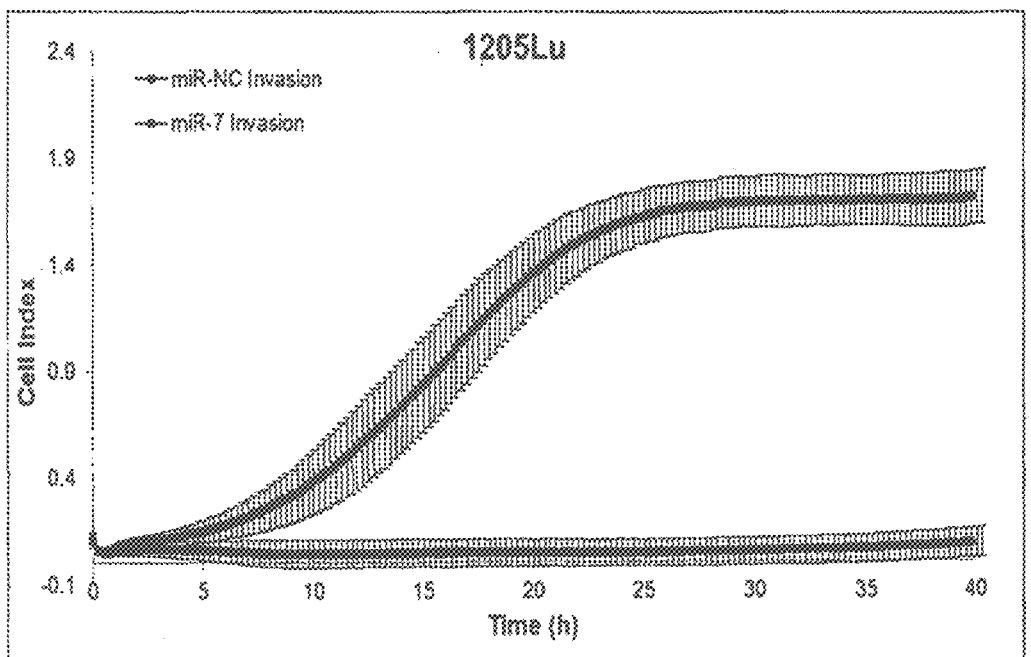

A further study was performed to further validate and extend these findings. Briefly, transient transfection was performed as described above to upregulate miR-7-5p expression in A2058, WM266-4, A375 and the highly metastatic 1205Lu melanoma cells and an xCELLigence system was then used to monitor cell migration and invasion in real-time. In each melanoma cell line, miR-7-5p overexpression significantly reduced, or even blocked, the rate of cell migration (FIGS. 5 and 7A) and invasion (FIGS. 6 and 7B) over a 20-25 hour period compared with a non-targeting, negative control miRNA (miR-NC). TaqMan miRNA RT-qPCR confirmed significant miR-7-5p overexpression in each melanoma cell line following transient transfection with miR-7-5p (data not shown).

Together, these results indicate that miR-7-5p inhibits the migration and invasion of melanoma cell lines in vitro.

Figure 8:
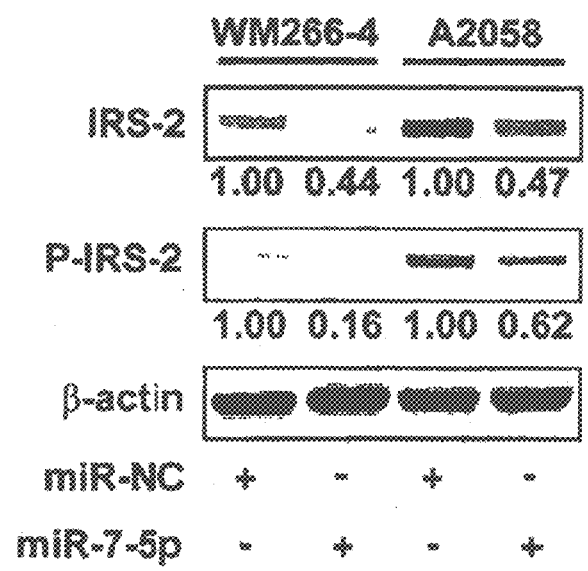
FIG. 8. IRS-2 is a target of miR-7-5p in melanoma cell lines. A. Western blot of IRS-2, P-IRS-2 and β-actin expression 72 hours after transfection of WM266-4 and A2058 cells with miR-7-5p or miR-NC. Densitometry was used to quantitate band intensity (values shown beneath each band). B. RT-qPCR of IRS-2 mRNA expression 24 hours after transfection of WM266-4 and A2058 cells with miR-7-5p or miR-NC. Data was normalised to GAPDH expression and expressed relative to miR-NC for each cell line. Error bars represent standard deviations. *, $p<0.001$; **, $p<0.01$.
Figure 8:
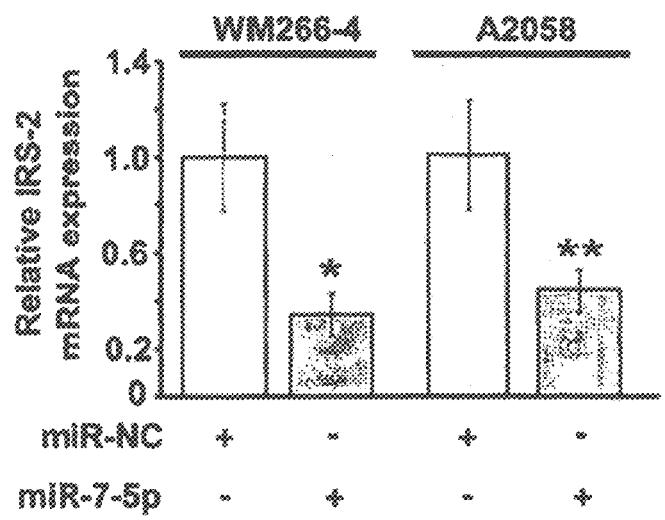

Example 5—Insulin Receptor Substrate-2 (IRS-2) is a Target of miR-7-5p in Melanoma Cell Lines The studies described in Example 1 indicated that miR-7-5p reduced expression of molecules in the IGFR1R pathway, including IRS-2. To confirm this, WM266-4 and A2058 melanoma cell lines were transfected with miR-7-5p or miR-NC, and IRS-2 mRNA and protein expression was assessed by RT-qPCR and immunoblotting, respectively. For each melanoma cell line, miR-7-5p reduced expression of IRS-2 protein, as well as the active form of IRS-2 (P-IRS-2) (FIG. 8A), and significantly decreased the levels of IRS-2 mRNA (FIG. 8B), suggesting that miR-7-5p promotes the degradation of IRS-2 mRNA in melanoma cell lines.

Example 6—IRS-2 Inhibition Decreases Akt Signaling and Melanoma Cell Migration To determine whether the capacity of miR-7-5p to inhibit melanoma cell migration and invasion in vitro is in part due to its regulation of IRS-2 expression, RNAi experiments were performed to knock down IRS-2 expression in WM266-4 melanoma cells. Briefly, WM266-4 melanoma cells were transfected with two commercially available, validated siRNAs against IRS-2 (si-IRS-2 #1, si-IRS-2 #2), and IRS-2, Akt and ERK1/2 expression, as well as WM266-4 cell migration, was assessed as described above.

Figure 9:
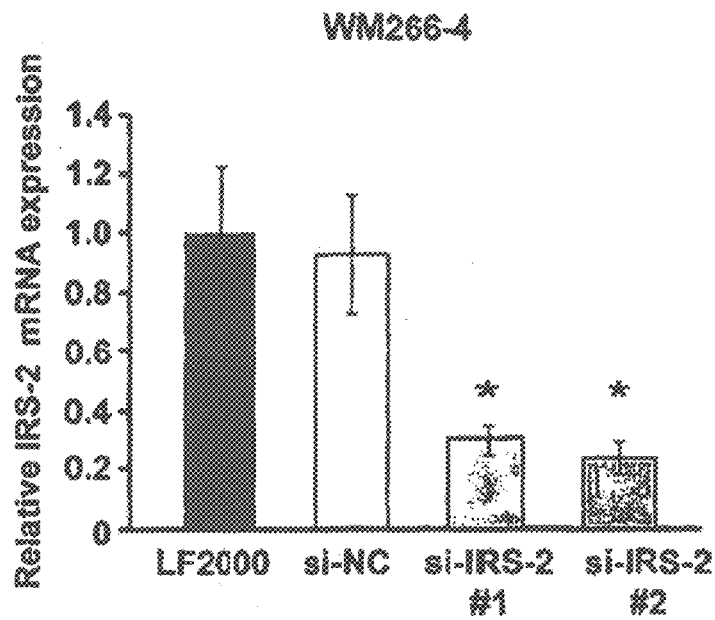
FIG. 9. IRS-2 RNAi-mediated knockdown inhibits Akt activity. A. RT-qPCR of IRS-2 mRNA expression 24 hours after transfection of WM266-4 cells with IRS-2 siRNAs (si-IRS-2 #1, si-IRS-2 #2) or NC siRNA (si-NC). Data was normalised to GAPDH expression and expressed relative to miR-NC for each cell line. Error bars represent standard deviations. *, $p<0.0002$. B. Western blot of IRS-2, P-IRS-2, Akt, P-Akt, ERK1/2, P-ERK1/2 and β-actin expression 72 hours after transfection of WM266-4 cells with IRS-2 siRNAs (si-IRS-2 #1, si-IRS-2 #2) or NC siRNA (si-NC). Duplicate bands are shown and densitometry was used to quantitate band intensity (mean intensity values shown beneath each set of duplicate bands).
Figure 9:
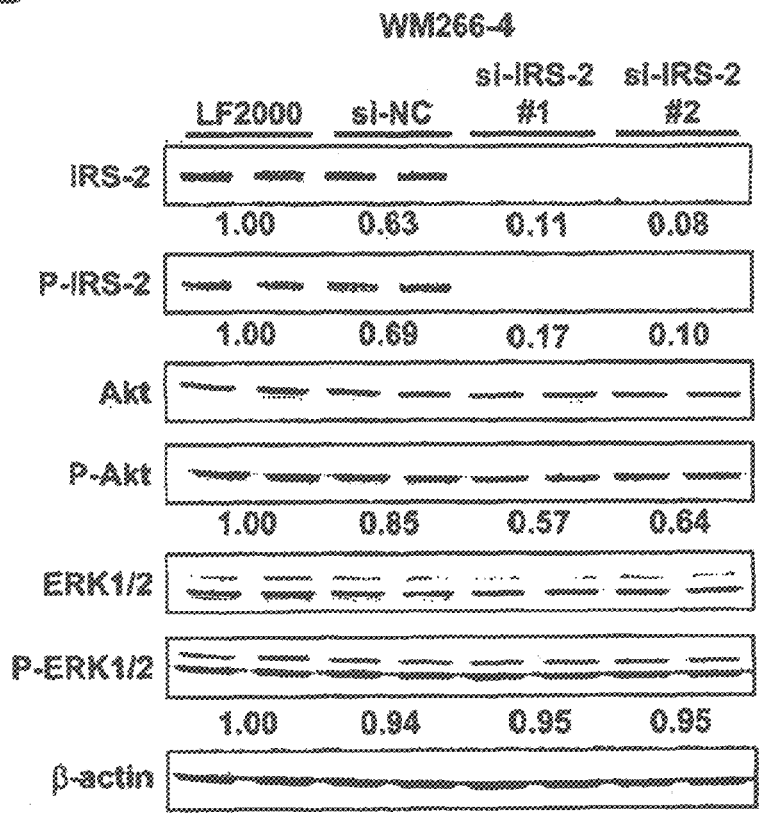

Transfection of WM266-4 melanoma cells with si-IRS-2 #1 or si-IRS-2 #2 resulted in significant reduction of both IRS-2 mRNA (FIG. 9A) and protein (FIG. 9B) expression, as well as the levels of P-IRS-2 (FIG. 9B), when compared with vehicle only (LF2000) or non-targeting siRNA (si-NC). Interestingly, the RNAi-mediated IRS-2 knockdown was accompanied with reduced activity of Akt (P-Akt; FIG. 9B), a key effector molecule downstream of IRS-2 and PI3K that regulates multiple oncogenic processes, including cell migration. This effect is consistent with the established role of IRS-2 in regulating PI3K activity (Shaw, 2001). In contrast, there was no significant effect of IRS-2 RNAi on the activity of ERK1/2 (P-ERK1/2; FIG. 9B).

Figure 10:
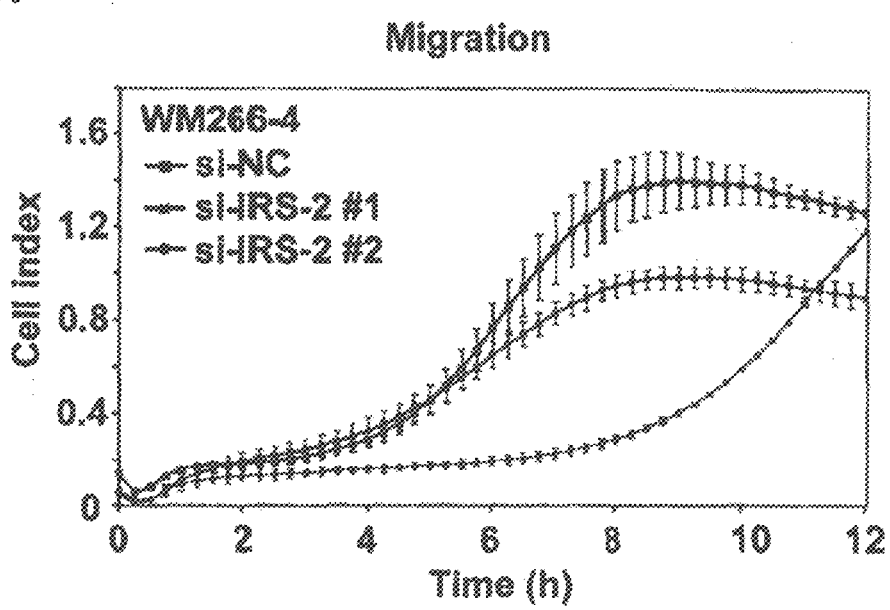
FIG. 10. IRS-2 RNAi-mediated knockdown inhibits melanoma cell line migration. A. Real time xCELLigence analysis of migration (represented by cell index) of WM266-4 melanoma cells following transfection with si-NC, si-IRS-2 #1, or si-IRS-2 #2. B. Graphical representation of the rate of migration (slope, 1/h) over 12 h for WM266-4 cells that were transfected with si-NC, si-IRS-2 #1, or si-IRS-2 #2.
Figure 10:
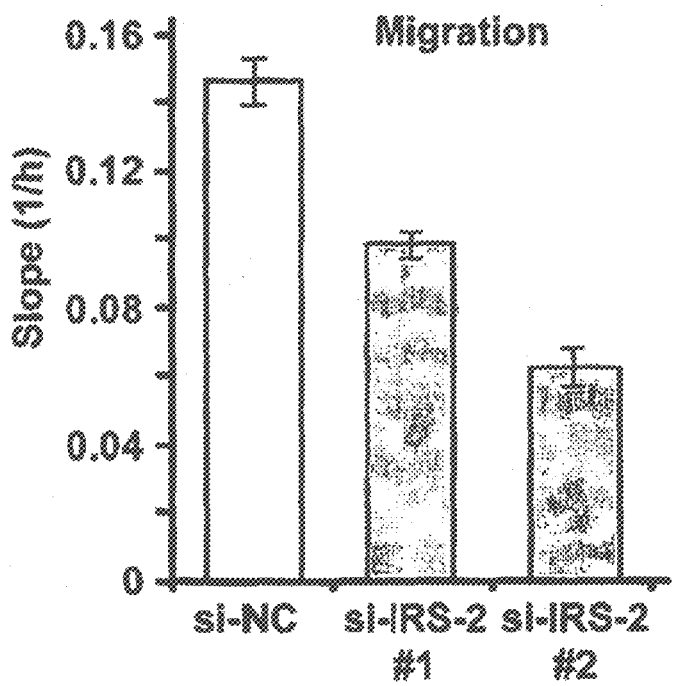

The migration and invasion of WM266-4 cells transfected with si-IRS-2 #1 or si-IRS-2 #2 was then assessed in real time with an xCELLigence instrument, as described above. The migration rate of WM266-4 cells was reduced following transfection of either si-IRS-2 #1 or si-IRS-2 #2, relative to si-NC (FIGS. 10A and B). IRS-2 RNAi-mediated knockdown of IRS-2 did not alter invasion of WM266-4 cells in vitro (data not shown). These data indicate that miR-7-5p inhibits the migration of metastatic melanoma cells at least in part by directly regulating the expression of IRS-2.

Example 7—miR-7-5p and PLX4032 Act Synergistically on Melanoma Cells

To further investigate the ability of miR-7-5p and BRAF inhibitors to act synergistically, the effect of the combination of miR-7-5p and the BRAF inhibitor PLX4032 on melanoma cell lines that display resistance to BRAF inhibitors was assessed.

Figure 11:
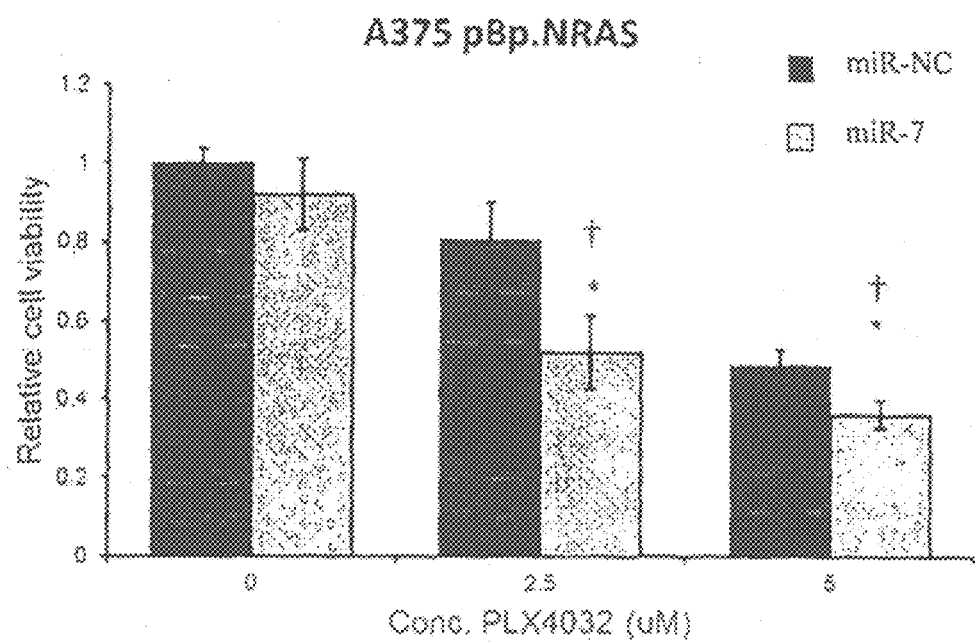
FIG. 11. miR-7-5p and PLX4032 act synergistically to inhibit melanoma cell proliferation. Cell titre analysis of A375 pBp.NRAS (A) or WM266-4 pBp.NRAS (B), each stably expressing a mutant Q61 NRAS gene that confers BRAF inhibitor resistance, following transfection with miR-7-5p or miR-NC and subsequent treatment with PLX4032. Data expressed relative to DMSO (vehicle)-treated/miR-NC-transfected cells and presented as mean±standard deviation. Synergy between the combination of miR-7-5p and PLX4032 was evaluated using the Bliss additivism model. † indicates synergy between miR-7-5p and PLX4032, and * indicates a significant difference between miR-NC and miR-7-5p at that concentration of PLX4032 (p-value<0.05).
Figure 11:
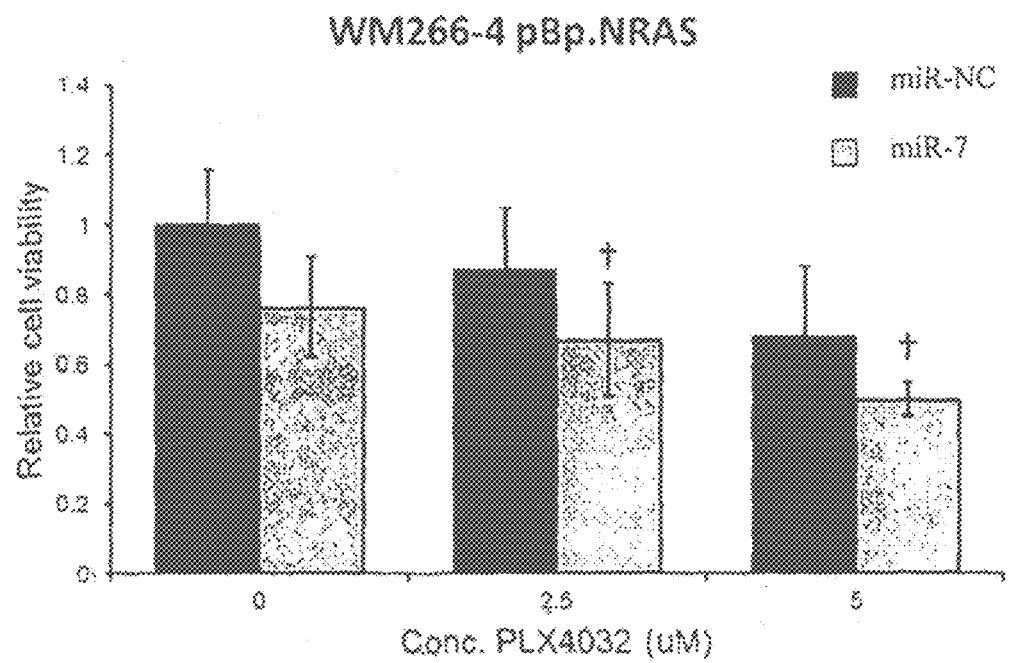

Briefly, melanoma cell lines A375 pBp.NRAS or WM266-4 pBp.NRAS, each stably expressing a mutant Q61 NRAS gene that confers BRAF inhibitor resistance, were reverse transfected with synthetic miR-7-5p or miR-NC precursor molecules (final concentration 1 nM; Ambion; Pre-miR-7 miRNA Precursor Product ID: PM10047; Pre-miR miRNA Precursor Negative Control #1, Product ID: AMI7110) and seeded at $5\times10^3$ cells/well in 96 well tissue culture plates. Three days after miRNA transfection, cells were treated with either DMSO (vehicle), 0.0001, 0.001, 0.01, 0.1, 1, 2.5, 5 or 10 µM PLX4032 (Selleck Chem, cat#S1267) for a further 4 days, at which point the number of viable cells in each well was assessed by MTS assay (CellTitre 96 Aqueous One Solution Cell Proliferation Assay Kit; Promega) according to the manufacturer's instructions. Data was expressed relative to DMSO (vehicle)-treated/miR-NC-transfected cells and presented as mean±standard deviation (SD). Synergy between the combination of miR-7-5p and PLX4032 was evaluated using the Bliss additivism model (see Bliss C, 1939). As shown in FIGS. 11A and B (showing only 0, 2.5 and 5 µM PLX4032 for clarity), miR-7-5p and PLX4032 acted synergistically to reduce the viability of both A375 pBp.NRAS and WM266-4 pBp.NRAS cells.

REFERENCES

Bliss C (1939) *Annals of Applied Biology* 26: 585-615

Chitnis, M, Yuen, J, Protheroe, A, Pollak, M and Macauley, V (2008) The type 1 insulin-like growth factor receptor pathway. *Clin Cancer Res* 14:6364-6370.

Giles K, Barker A, Zhang P M, Epis M R and Leedman P J (2011) MicroRNA regulation of growth factor receptor signaling in human cancer cells. *Methods Mol Biol* 676: 147-163.

Girnita A, Girnita L, Prete Fd, Bartolazzi A, Larsson O and Axelson M (2004) Cyclolignans as inhibitors of the insulin-iike growth factor-1 receptor and malignant cell growth. *Cancer Res* 64:236-242.

Jiang L, Liu X, Chen Z, Jin Y, Heidbreder C E, Kolokythas A, Wang A, Dai Y and Zhou X (2010) MicroRNA-7 targets IGF1R (insulin-like growth factor 1 receptor) in tongue squamous cell carcinoma cells. *Biochem J* 432: 199-205.

Meier F, Schittek B, Busch S, Garbe C, Smalley K, Satyamoorthy K, Li G and Herlyn M (2005) The RAS/RAF/MEK/ERK and PI3K/AKT signaling pathways present molecular targets for the effective treatment of advanced melanoma. *Front Biosci* 10:2986-3001.

Mhaidat N M, Zhang X D, Allen J, Avery-Kiejda K A, Scott R J and Hersey P (2007) Temozolomide induces senescence but not apoptosis in human melanoma cells. *Br J Cancer* 97:1225-1233.

Mukohara T, Shimada H, Ogasawara N, Wanikawa R, Shimomura M, Nakatsura T, Ishii G, Park J O, Jänne P A, Saijo N and Minami H (2009) Sensitivity of breast cancer cell lines to the novel insulin-like growth factor-1 receptor (IGF-1R) inhibitor NVP-AEW541 is dependent on the level of IRS-1 expression. *Cancer Lett* 282:14-24.

Sosman J A, Kim K B, Schuchter L, Gonzalez R, Pavlick A C, Weber J S, McArthur G A, Hutson T E, Moschos S J, Flaherty K T, Hersey P, Kefford R, Lawrence D, Puzanov I, Lewis K D, Amaravadi R K, Chmielowski B, Lawrence H J, Shyr Y, Ye F, Li J, Nolop K B, Lee R J, Joe A K and Ribas A (2012) Survival in BRAF V600-mutant advanced melanoma treated with vemurafenib. *N Engl J Med* 366: 707-714.

Shaw (2001) Identification of Insulin Receptor Substrate 1 (IRS-1) and IRS-2 as Signaling Intermediates in the α6β4 Integrin-Dependent Activation of Phosphoinositide 3-OH Kinase and Promotion of Invasion, *Mol Cell Biol* 21: 5082-5093

Stracke M L, Engel J D, Wilson L W, Rechler M M, Liotta L A and Schiffmann E (1989) The type I insulin-like growth factor receptor is a motility receptor in human melanoma cells. *J Biol Chem* 264:21544-21549.

Villanueva J, Vultur A, Lee J T, Somasundaram R, Fukunaga-Kalabis M, Cipolla A K, Wubbenhorst B, Xu X, Gimotty P A, Kee D, Santiago-Walker A E, Letrero R, D'Andrea K, Pushparajan A, Hayden J E, Brown K D, Laquerre S, McArthur G A, Sosman J A, Nathanson K L and Herlyn M (2010) Acquired resistance to BRAF inhibitors mediated by a RAF kinase switch in melanoma can be overcome by cotargeting MEK and IGF-1R/PI3K. *Cancer Cell* 18:683-695.

Yang H, Higgins B, Kolinsky K, Packman K, Go Z, Iyer R, Kolis S, Zhao S, Lee R, Grippo J F, Schostack K, Simcox M E, Heimbrook D, Bollag G and Su F (2010) RG7204 (PLX4032), a selective BRAF V600E inhibitor, displays potent antitumor activity in preclinical melanoma models. *Cancer Res* 70:5518-5527.

The invention claimed is:

1. A synergistic composition for the treatment of a cancer or tumour expressing IGF1R or a constituent of an IGF1R signaling pathway, the composition comprising a miR-7-5p miRNA, a precursor thereof or a miRNA comprising a seed region comprising the sequence GGAAGA, and at least one of a BRAF inhibitor, an IGF1R inhibitor and a DNA alkylating chemotherapeutic agent.

2. The composition of claim 1, wherein the cancer is melanoma.

3. The composition of claim 1, wherein the melanoma is malignant melanoma.

4. The composition of claim 2, wherein the melanoma comprises cells expressing a mutation in one or more of BRAF, NRAS or PTEN.

5. The composition of claim 1, wherein the miR-7-5p miRNA is hsa-miR-7-5p comprising the nucleotide sequence set forth in SEQ ID NO:1.

6. The composition of claim 1, wherein the miR-7-5p miRNA precursor is selected from hsa-miR-7-1, hsa-miR-7-2 and hsa-miR-7-3, comprising a sequence as set forth in any one of SEQ ID Nos:2 to 4.

7. The composition of claim 1, wherein the BRAF inhibitor is a mutant BRAF—specific inhibitor or mutant BRAF—selective inhibitor.

8. The composition of claim 7, wherein the mutant BRAF comprises the V600E mutation.

9. The composition of claim 7, wherein the BRAF inhibitor is PLX4032 (vemurafenib).

10. The composition of claim 1, wherein the IGF1R inhibitor is a tyrosine kinase inhibitor selected from picropodophyllin (PPP) and NVP-AEW541.

11. The composition of claim 1, wherein the chemotherapeutic agent is temozolomide (TMZ).

* * * * *